United States Patent [19]
Ksander et al.

[11] Patent Number: 5,977,075
[45] Date of Patent: Nov. 2, 1999

[54] N-AROYLAMINO ACID AMIDES AS ENDOTHELIN INHIBITORS

[75] Inventors: Gary Michael Ksander, Milford; Paivi Jaana Kukkola, Morristown; Leslie Anne Robinson, Warren, all of N.J.

[73] Assignee: Novartis AG, Basel, Switzerland

[21] Appl. No.: 08/945,329

[22] PCT Filed: Apr. 11, 1996

[86] PCT No.: PCT/EP96/01547

§ 371 Date: Oct. 21, 1997

§ 102(e) Date: Oct. 21, 1997

[87] PCT Pub. No.: WO96/33170

PCT Pub. Date: Oct. 24, 1996

Related U.S. Application Data

[63] Continuation-in-part of application No. 08/426,351, Apr. 21, 1995, abandoned.

[51] Int. Cl.$^6$ .................................................. A61K 38/05
[52] U.S. Cl. .............................................. 514/19; 562/445
[58] Field of Search ................................ 514/19; 562/445

[56] References Cited

U.S. PATENT DOCUMENTS

| | | |
|---|---|---|
| 4,339,534 | 7/1982 | Johansen . |
| 5,273,990 | 12/1993 | De Lombaert .......................... 514/381 |

FOREIGN PATENT DOCUMENTS

| | | |
|---|---|---|
| 333174 | 9/1989 | European Pat. Off. . |
| 457 195 A2 | 11/1991 | European Pat. Off. . |
| 457195 | 11/1991 | European Pat. Off. . |
| 460 679 A2 | 12/1991 | European Pat. Off. . |
| 460679 | 12/1991 | European Pat. Off. . |
| 555537 | 8/1993 | European Pat. Off. . |
| 9512611 | 5/1995 | WIPO . |
| 9526360 | 10/1995 | WIPO . |

OTHER PUBLICATIONS

Derwent Abstract DE 3332633 A1 of Apr. 4, 1985, and pp. 18–22 of DE 3332633 (see formulae I and II referred to in abstract).

Jordan, et al., Heterocycles, vol. 33, No. 8, Apr. 1992, pp. 657–671.

Derwent Abstract 85–087758[15], 1986.

*Primary Examiner*—Cecilia J. Tsang
*Assistant Examiner*—David Lukton
*Attorney, Agent, or Firm*—Norbert Gruenfeld

[57] ABSTRACT

The present invention relates to the compounds of formula (I)

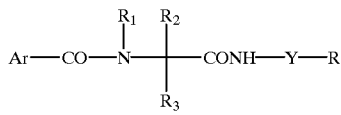

wherein R is carboxy, esterified carboxy, carbamoyl, N-(alkyl or aryl)-carbamoyl, cyano, 5-tetrazolyl or $CONH-SO_2-R_4$; $R_1$ is hydrogen, lower alkyl, aryl-lower alkyl or cycloalkyl-lower alkyl; $R_2$ is hydrogen or lower alkyl, or $R_1$ and $R_2$ represent lower alkylene to form together with the carbon and nitrogen atoms to which they are attached an azacycloalkane ring; $R_3$ is heterocyclic or carbocyclic (aryl or biaryl)-lower alkyl; Y is lower alkylidenyl, 3- to 10-membered cycloalkylidenyl which may be substituted by oxo, alkylenedioxy, hydroxy, acyloxy, lower alkoxy; or Y is 5- to 10-membered cycloalkylidenyl fused to a saturated or unsaturated carbocyclic 5- or 6-membered ring; or Y is 5- to 8-membered oxacycloalkylidenyl, 5- to 8-membered (thia-, oxothia- or dioxothia-) cycloalkylidenyl, or 5- to 8-membered azacycloalkylidenyl optionally N-substituted by lower alkyl or aryl-lower alkyl; $R_4$ represents hydrogen, lower alkyl, carbocyclic aryl, heterocyclic aryl, cycloalkyl, (carbocyclic aryl, heterocyclic aryl, cycloalkyl, hydroxy, acyloxy, or lower alkoxy)-lower alkyl, lower alkyl substituted by carboxyl, by esterified carboxyl or by amidated carboxyl; Ar represents carbocyclic or heterocyclic aryl; and pharmaceutically acceptable salts thereof; which are useful as endothelin inhibitors in mammals.

17 Claims, No Drawings

N-AROYLAMINO ACID AMIDES AS ENDOTHELIN INHIBITORS

CROSS REFERENCE TO RELATED APPLICATIONS

This application is a continuation-in-part of application Ser. No. 08/426,351 filed Apr. 21, 1995, now abandoned.

The present invention relates to acyl-amino acid derivatives of formula I below useful as endothelin (ET) receptor antagonists, in particular ET-1 antagonists, methods for preparation thereof, pharmaceutical compositions comprising said compounds, a method of inhibiting endothelin activity in mammals and a method of treating endothelin dependent diseases or conditions in mammals using such compounds or pharmaceutical compositions comprising such compounds.

Endothelin has been implicated in the pathogenesis of various diseases and elevated levels of endothelin have been reported in such diseases. Endothelin is a potent vasoconstrictor and is also known to be, inter alia, a potent constrictor of mammalian bronchial tissue.

Thus the endothelin receptor antagonists of the instant invention can be used for the treatment of endothelin dependent diseases, including various cardiovascular diseases such as cerebral and coronary vasospasm, cerebral and coronary ischemia, subarachinoidal hemorrhage, various types of hypertension, pulmonary hypertension, cardiac failure, Raynaud-syndrome, diabetes, artherosclerosis or restenosis following angioplasty, and also for the treatment of asthma, renal failure, dialysis, glomerular injury, hepatic failure, stomach and duodenal ulcer, ulcus cruris, various brain dysfunctions including migraine, benign prostatic hyperplasia, and ocular diseases such as glaucoma.

DETAILED DESCRIPTION OF THE INVENTION

The present invention relates to the compounds of formula I

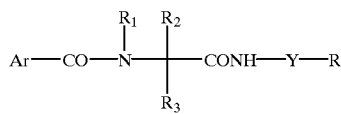

wherein R is carboxy, esterified carboxy, carbamoyl, N-(alkyl or aryl)-carbamoyl, cyano, 5-tetrazolyl or $CONH-SO_2-R_4$;

$R_1$ is hydrogen, lower alkyl, aryl-lower alkyl or cycloalkyl-lower alkyl;

$R_2$ is hydrogen or lower alkyl, or $R_1$ and $R_2$ represent lower alkylene to form together with the carbon and nitrogen atoms to which they are attached an azacycloalkane ring;

$R_3$ is heterocyclic or carbocyclic (aryl or biaryl)-lower alkyl;

Y is lower alkylidenyl, 3–10 membered cycloalkylidenyl which may be substituted by oxo, alkylenedioxy, hydroxy, acyloxy, lower alkoxy; or Y is 5–10 membered cycloalkylidenyl fused to a saturated or unsaturated carbocyclic 5- or 6-membered ring; or Y is 5 to 8 membered oxacycloalkylidenyl, 5 to 8 membered (thia-, oxothia- or dioxothia-) cycloalkylidenyl, or 5- to 8-membered azacycloalkylidenyl optionally N-substituted by lower alkyl or aryl-lower alkyl;

$R_4$ represents hydrogen, lower alkyl, carbocyclic aryl, heterocyclic aryl, cycloalkyl, (carbocyclic aryl, heterocyclic aryl, cycloalkyl, hydroxy, acyloxy, or lower alkoxy)-lower alkyl, lower alkyl substituted by carboxyl, by esterified carboxyl or by amidated carboxyl;

Ar represents carbocyclic or heterocyclic aryl; and pharmaceutically acceptable salts thereof.

The compounds of the present invention possess one or more chiral centers. The instant invention includes the possible isomers and enantiomers. Preferred are the compounds of formula I in which the carbon atom to which $R_2$ and $R_3$ are attached has the R-configuration corresponding to the D-amino acid.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, amino, lower alkanoylamino, lower alkyl-(thio, sulfinyl or sulfonyl), lower alkoxycarbonyl, mono- or di-lower alkylcarbamoyl, mono- or di-lower alkylamino, pyrrolidino, piperidino, morpholino.

Bicyclic carbocyclic aryl represents 1- or 2-naphthyl or 1- or 2-naphthyl preferably substituted by lower alkyl, lower alkoxy or halogen.

Heterocyclic aryl represents, for example, mono- or bicyclic heteroaryl having up to and including 4 identical or different hetero atoms such as nitrogen, oxygen or sulfur, preferably one, two, three, or four nitrogen atoms, a nitrogen and an oxygen or a sulfur, an oxygen or a sulfur atom. Preferred are corresponding 5- or 6-membered monocyclic heteroaryl radicals which may also be attached to a carbocyclic aryl radical, especially phenyl. Appropriate monocyclic 5-membered heteroaryl radicals are, for example, monoaza-, diaza-, -triaza-, tetraaza-, monooxa-, monothia-, oxaza- or thiaza-cyclic aryl radicals, whereas an appropriate monocyclic 6-membered radical is in particular an azaaryl or an oxaaryl radical such as pyridyl or pyranyl. A corresponding monocyclic heteroaryl radical includes, for example, thienyl such as 2- or 3-thienyl, furanyl such as 2- or 3-furanyl, pyrrolyl such as 1-, 2- or 3-pyrrolyl, triazolyl such as 1,3,5-1H-triazol-2-yl or 1,3,4-triazol-2-yl, tetrazolyl such as 1H-tetrazol-5-yl, imidazolyl such as 1-, 2-, 4- or 5-imidazolyl, oxazolyl such as 2-, 4- or 5 oxazolyl, isoxazolyl such as 3-, 4- or 5-isoxazolyl, thiazolyl such as 2-, 4- or 5-thiazolyl, isothiazolyl such as 3-, 4- or 5-isothiazolyl, pyridyl such as 2-, 3- or 4-pyridyl, pyranyl such as 2- or 3-pyranyl and pyrimidinyl such as 2-pyrimidinyl. The heteroaryl group may be unsubstituted, or mono- or poly-, for example di- or trl-substituted. The substituents for the heteroaryl group are, for example, those described for the aryl group above. A substituted heteraryl is, for example, 3-methyl-2-thienyl, and 5-methyl-2-thienyl.

Bicyclic heterocyclic aryl represents bicyclic heteroaryl, for example, a benzo-fused 5- or 6-membered heteroarylradical. A corresponding radical includes, for example, indolyl such as 2- or especially 3-indolyl, 1-lower alkylindolyl such as 1-methyl-3-indolyl, benzothiophenyl such as 2- or especially 3-benzothiophenyl, benzofuranyl such as 2- or 3-benzofuranyl, quinolinyl such 2-, 3- or especially 4-quinolinyl, and isoquinolinyl such as 1-, 3- or 4-isoquinolinyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, acylamino, lower alkoxycarbonyl, amino, mono- or dialkylamino, pyrrolidino, piperidino, morpholino or acylamino; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen, trifluoromethyl, amino, mono- or dialkylamino, pyrrolidino, piperidino, morpholino or acylamino.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkylene group preferably contains 1–4 carbon atoms and represents for example ethylene, propylene, butylene.

A lower alkoxy group preferably contains 1–4 carbon atoms and represents for example methoxy, propoxy, isopropoxy or advantageously ethoxy.

Cycloalkyl represents a saturated cyclic hydrocarbon radical which preferably contains 3 to 10 ring carbons, preferably cyclopropyl, cyclopentyl or cyclohexyl.

The term cycloalkyl(lower)alkyl represents preferably 1- or 2-(cyclopentyl or cyclohexyl)-ethyl, 1-, 2- or 3-(cyclopentyl or cyclohexyl)propyl, or 1-, 2-, 3- or 4-(cyclopentyl or cyclohexyl)-butyl.

A lower alkoxycarbonyl group preferably contains 1 to 4 carbon atoms in the alkoxy portion and represents, for example, methoxycabonyl, propoxycarbonyl, isopropoxycarbonyl or advantageously ethoxycarbonyl.

Cycloalkylidenyl is 3- to 10-membered, preferably 3-, 5- or 6-membered, and represents a cycloalkane linking group in which the two attached groups are attached to the same carbon of the cycloalkane ring, such as cyclopropylidenyl, cyclopentylidenyl or cyclohexylidenyl and the like which may be substituted by oxo, hydroxy, lower alkoxy, acyloxy, lower alkylene-dioxy, or lower alkyl.

Cycloalkylidenyl fused to a saturated carbocyclic ring represents e.g. perhydronaphthylidenyl.

Cycloalkylidenyl fused to an unsaturated carbocyclic ring represents preferably benzo fused cycloalkylidenyl, e.g. 1,1- or2,2-tetralinylidenyl or 1,1- or 2,2-indanylidenyl.

5- to 8-Membered oxacycloalkylidenyl represents preferably a tetrahydrofuran or tetrahydropyran linking group in which the two attached groups are attached to the same carbon atom of the respective rings, e.g. at the 3 or 4 position thereof.

5- to 8-Membered thiacycloalkylidenyl represents preferably a tetrahydrothiophene or tetrahydrothiopyran linking group in which the two attached groups are attached to the same carbon atom of the respective rings, e.g. at the 3- or 4-position thereof, and sulfoxide and sulfonyl versions thereof.

5- to 8-Membered azacycloalkylidenyl represents preferably a pyrrolidine or piperidine linking group in which the two attached groups are attached to the same carbon atom of the respective rings, e.g. at the 3- or 4-position thereof, and the nitrogen may be substituted by lower alkyl, e.g. methyl, or by aryl-lower alkyl, e.g. benzyl.

An azacycloalkane ring is preferably pyrrolidine or piperidine.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl.

Lower alkanoyl is preferably acetyl, propionyl, butyryl, or pivaloyl.

Optionally substituted lower alkanoyl for example represents lower alkanoyl or lower alkanoyl substituted by lower alkoxycarbonyl, lower alkanoyloxy, lower alkanoyltio, lower alkoxy, or by lower alkylthio.

Aroyl is preferably monocyclic carbocyclic or monocyclic heterocyclic aroyl.

Monocyclic carbocyclic aroyl is preferably benzoyl or benzoyl substituted by one or more of lower alkyl, lower alkoxy, hydroxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocylic aroyloxy or monocyclic heterocyclic aroyloxy.

Biaryl represents monocarbocyclic carbocyclic or heterocyclic aryl substituted, preferably at the para position, by monocyclic carbocyclic or monocyclic heterocyclic aryl.

Especially preferred as biaryl in biaryl-lower alkyl ($R_3$ in formula I) are 5- or 6-membered monocyclic heteroaryl radicals which are attached to a carbocyclic radical and comprise, for example, pyridyl-phenyl such as 4-(2-pyridyl)-phenyl, thienyl-phenyl, such as 2-thienyl-4-phenyl or 3-thienyl-4-phenyl, furyl-phenyl such as 2-furyl-4-phenyl or 3-furyl-4-phenyl, pyrrolylphenyl such as 1-, 2- or 3-pyrrolyl-4-phenyl, imidazolyl-phenyl such as 1-, 3- or 5-imidazolyl-4-phenyl, oxazolylphenyl such as 2-, 4- or 5-oxazolyl-4-phenyl, isoxazolyl-phenyl such as 5-isoxazolyl-4-phenyl, thiazolyl-phenyl such as 2-, 4- or 5-thiazolyl-phenyl, iso-thiazolyl-phenyl such as 3-, 4- or 5-isothiazolyl-phenyl, triazolyl-phenyl such as 1,3,5-1H-triazol-2-yl-4-phenyl or 1,3,4-triazol-2-yl-4-phenyl, tetrazolyl-phenyl such 5-1H-tetrazolyl-4-phenyl; also phenylpyrimidinyl such as 2-phenyl-5-pyrimidinyl. Preferred is 4-(heteroaryl)-phenyl.

Esterified carboxyl is preferably lower alkoxycarbonyl, aryl-lower alkoxycarbonyl and the like.

Amidated carboxyl is preferably carbamoyl, mono- or dialkylcarbamoyl, mono- or di-(aryl-lower alkyl)carbamoyl and the like.

Alkylenedioxy is preferably methylenedioxy or ethylenedioxy.

Preferred are the compounds of formula I wherein R is carboxy, 5-tetrazolyl, esterified carboxy or CONH—SO$_2$—R$_4$; R$_1$ is C$_1$–C$_4$-alkyl; R$_2$ hydrogen; or R$_1$ and R$_2$ together represent C$_3$–C$_5$-alkylene; R$_3$ is monocyclic carbocyclic or heterocyclic aryl-lower alkyl or biaryl-lower alkyl in which biaryl is monocyclic carbocyclic or heterocyclic aryl substituted by monocyclic carbocyclic or heterocyclic aryl; Y is 3–10-membered cycloalkylidenyl or 5–10-membered cycloalkylidenyl fused to an unsaturated carbocyclic 6-membered ring, 5–8-membered oxacycloalkylidenyl, or 5–8-membered (thia, oxothia or dioxothia)-cycloalkylidenyl; R$_4$ represents monocyclic carbocyclic aryl, monocyclic carbocyclic aryl-lower alkyl, lower alkyl, cycloalkyl, carboxy-lower alkyl or lower alkoxycarbonyl-lower alkyl; and Ar is carbocyclic or heterocyclic monocyclic aryl; and pharmaceutically acceptable salts thereof.

Further preferred are the compounds of formula I wherein Ar is monocyclic carbocyclic aryl such as 3-or 4-methylphenyl, 3,5-dimethylphenyl, 3,5-difluorophenyl, 3,5-dichlorophenyl, 3,5-dibromophenyl, 3,5-di-trifluoro methyl-phenyl, 3,5-dihydroxyphenyl, 2,5-dihydroxyphenyl, 2-, 3- or 4-methoxyphenyl, 3,5-dimethoxyphenyl, 3-hydroxy-5-methyl phenyl, monocyclic heterocyclic aryl such as pyridyl, pyrimidyl or thienyl, each optionally substituted by lower alkyl; $R_1$ is $C_1$–$C_3$-alkyl, in particular methyl; $R_2$ is hydrogen; or $R_1$ and $R_2$ together represent propylene or butylene; $R_3$ is arylmethyl or biarylmethyl, in particular 4-pyrrolidino-benzyl, 4-piperidino-benzyl, 4-(1-pyrrolyl)-benzyl, 4-(5-isoxazolyl) benzyl, 4-(3-thienyl) benzyl, 4-(2-thienyl)benzyl, 4-biphenylylmethyl, 4-(2-pyridyl)benzyl; Y is cyclopropylidenyl, cyclopentylidenyl, indanylidenyl, 4-tetra hydro-4H-pyranylidenyl, cyclohexylidenyl, 4-tetrahydro-4H-pyranylidenyl, 4-ethylenedi oxycyclohexylidenyl or 4-oxocyclohexylidenyl; R is carboxy, lower alkoxycarbonyl, 5-tetrazolyl, or CONH—$SO_2$—$R_4$; $R_4$ in CONH—$SO_2$—$R_4$ represents lower alkyl, phenyl, benzyl, lower alkoxycarbonyl-lower alkyl or carboxy-lower alkyl; and pharmaceutically acceptable salts thereof.

A particular embodiment of the invention relates to the compounds of formula II

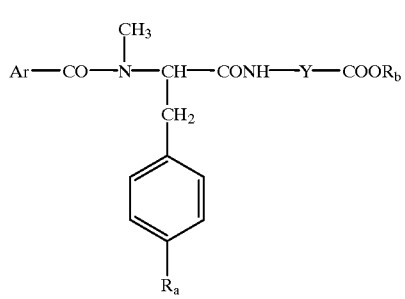

(II)

wherein Ar is phenyl optionally substituted by one or two of lower alkyl, halo, hydroxy, lower alkoxy or trifluoromethyl; $R_a$ is 1-pyrrolyl, 5-isoxazolyl, 2-thienyl, 3-thienyl or phenyl; $R_b$ is hydrogen, lower alkyl or aryl-lower alkyl; Y is cyclopropylidenyl, cyclopentylidenyl, indanylidenyl, 4-tetrahydro-4H-pyranylidenyl, cyclo hexylidenyl, 4-tetrahydro-4H-thio-pyranylidenyl, or 4-ethylenedioxycyclohexylidenyl; and pharmaceutically acceptable salts thereof.

A preferred embodiment of the invention relates to compounds of formula III

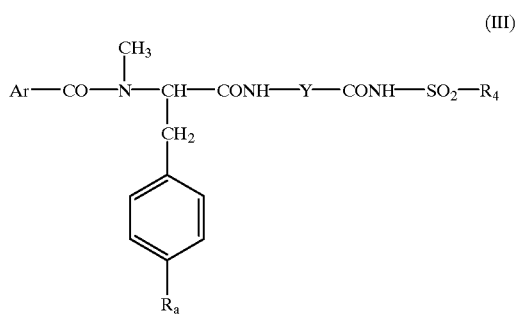

(III)

wherein Ar is phenyl optionally substituted by one or two of lower alkyl, halo, hydroxy, lower alkoxy or trifluoromethyl; $R_a$ is 1-pyrrolyl, 5-isoxazolyl, 2-thienyl, 3-thienyl or phenyl; and $R_4$ is lower alkyl; Y is cyclopropylidenyl, cyclopentylidenyl, indanylidenyl, 4-tetrahydro4H-pyranylidenyl, cyclo hexylidenyl, 4-tetrahydro-4H-thio-pyranylidenyl, or 4-ethylenedioxycyclohexylidenyl; and pharmaceutically acceptable salts thereof.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxy methyl)-ammonium salts.

The compounds of the invention are useful for inhibiting or blocking endothelin receptor activity in mammals.

The compounds of the invention are thus useful for the treatment of endothelin dependent disorders or conditions in mammals, e.g. cardiovascular and pulmonary disorders, such as hypertension, renal failure, myocardial infarction and bronchial asthma.

The compounds of the invention exhibit endothelin antagonist activity at $ET_A$ and/or $ET_B$ receptors and are also useful as positive controls in tests for the evaluation and discovery of new potential endothelin antagonists.

The above-cited properties are demonstrable in vitro and in vivo tests, using advantageously mammals, e.g. swines, rats, guinea pigs, dogs, rabbits, or isolated organs and tissues, as well as mammalian enzyme preparations. Said compounds can be applied in vitro in the-form of solutions, e.g. preferably aqueous solutions, and in vivo either enterally or parenterally, advantageously intravenously e.g. in aqueous solution. The dosage in vitro may range between about $10^{-5}$ molar and $10^{-10}$ molar concentrations. The dosage in vivo may range, depending on the route of administration, between about 0.01 and 100 mg/kg.

The beneficial biological effects can be determined in tests already generally known in the art. For instance the $ET_A$ receptor inhibitory activity can be determined by measuring the release of [$^3$H]-inositol from [$^3$H]-inositol labeled A7r5 cells, as described by Cioffi et al, J. Cardiovasc. Pharmacol. 22 (Suppl. 8), S-168 (1993). Also the inhibition of the binding of [$^{125}$I] ET-1 to porcine thoracic aorta membranes ($ET_A$ receptor) can be determined according to Cioffi et al, J. Pharmacol. Exp. Ther. 262, 611 (1992); similarly inhibition of binding of [$^{125}$I] ET-1 to rat cerebellum membranes ($ET_B$ receptor).

The effects of endothelin inhibitory activity can be determined e.g. by measuring the effect of a 30 minute pretreatment with test compound (0.1–10 mM) on the ET-1 induced contractile response in isolated tissues such as rabbit aorta. Similar pretreatment with test compound is utilized to determine the effects of phenylephrine or KCl induced contraction, an indication that the specificity of hemodynamic affects is caused by interaction with the endothelin receptor.

1. Binding Studies—$ET_A$ and $ET_B$;

Chinese hamster ovary cells expressing human $ET_A$ (CHO-ETA) or $ET_B$ (CHO-ETB) receptors are cultured in F12 medium (cibcoBRL, Grand Island, N.Y.) containing 10% fetal bovine serum and 1× antibiotic-antimycotic (GibcoBRL). Cells are harvested, then centrifuged, and finally homogenized in buffer containing 1 mM EDTA and 10 nM Tris, pH 8.0. The cell debris is removed by brief centrifugation, and then the supernatant centrifuged again at 50,000×g for 10 minutes. The resulting pellet is resuspended in Hanks' balanced salt solution at a protein concentration of 0.2 mg/mg and stored in aliquots at −80° C. Competition binding is carried out by in incubating 0.2–1.0 mg of membrane protein from CHO-$ET_A$ or CHO-$ET_B$ cells with 12,000 cpm [$^{125}$I] ET-1 (New England Nuclear, Boston, Mass.) with or without the competing ligand for 2 hours at 37° C. in a buffer containing 0.2 mg/ml bovine serum albumin, 0.002% Triton X-100, 0.02% NaN$_3$, and 50 nM Tris, pH 7.0. The reaction is terminated by filtration through a cell harvester (Brandel, Gaitherburg, Md.) using GF/C filters. Triplicate samples are carried out in each experiment, and if appropriate, the full dose-response curve for each competing ligand is performed at least three times. An IBM-compatible version of ALLFIT (Am. J. Physiol. 1978; 235:E97–102) is used to fit data to a single interactive site model for the determination of IC$_{50}$ values.

Illustrative of the invention, the compounds of example 1 and example 2(aa) have an IC$_{50}$ of less than 1 nM for both ET$_A$ and ET$_B$ binding.

2. Isolated Tissue Studies

Studies measuring isometric tension are carried out according to the procedure of Shetty et al. (Biochem. Biophys. Res. Comm. 1993; 191:459–464). Saphenous veins (for antagonism of ET$_B$) are obtained from mongrel dogs which are anesthetized with pentobarbital. Thoracic aortas are obtained from Sprague-Dawley male rats (for antagonism of ET$_A$). Coronary arteries are obtained from porcine hearts. Tissue segments (4–5 mm) from each vascular preparation are equilibrated for 90 minutes during which time the tissues are adjusted to a preload tension of 2 gm, except for the porcine coronary which is adjusted to 4 gm preload. Concentration-response curves are generated by the cumulative addition of the peptides. Antagonists are added 30 minutes prior to the addition of ET-1 or STX6c. Contractions are expressed as a percentage of the response to 80 nM KCl. Relaxation is quantitated by expressing the tension after relaxation as a percent of the tension induced by 1 mM phenylephrine.

Illustrative of the invention, the compounds of example 1 and example 2(aa) inhibit ET-induced contractile response in dog saphenous veins and thoracic aorta isolated tissue preparations.

3. Cardiovascular Studies

Male Sprague-Dawley rats (250 gm) are anesthetized with Inactin (100 mg/kg, i.p.). The left femoral artery and vein are exposed and cannulated for the measurement of arterial blood pressure and injection of drugs, respectively. The left renal artery is exposed and a pulsed Doppler flow proble (Iowa Doppler Products, Iowa City, Iowa) is placed on the artery for the measurement of renal blood flow according to the procedure of Haywood et al. (Am. J. Physiol. 1981; 242:H273–278). Velocity measurements are made optimal by adjusting the Doppler flowmeter signals (model 545C, Bioeng. Dept., Univ. of Iowa) until peak voltage displacement (analogous to Doppler shift) is achieved. Signals are recorded as a mean flow velocity of a Doppler shift (kHz) on a Grass Polygraph (Grass Instruments, Quincy, Mass., USA). Flow is allowed to equilibrate for 60 minutes before beginning the experiment. Renal vascular resistance (RVR) is calculated as the ratio of mean arterial pressure (MAP) and renal blood flow.

ET-1 (0.25 nmol/kg, i.v.) and IRL 1620 (0.5 nmol/kg, i.v.) are administered to the rats 15 minutes after dosing with the test compounds. Mean arterial pressure (MAP) is measured at the peak of the vasodilator response and at 5 minutes after dosing. Renal vascular resistance (RVR) is determined also at 5 minutes after dosing.

The compounds of formula I can be prepared e.g.

(a) by reacting a carboxylic acid of formula IV

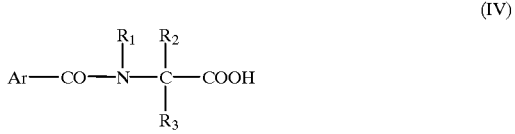

(IV)

wherein Ar, R$_1$, R$_2$ and R$_3$ have meaning as defined above, or a reactive derivative thereof with a compound of the formula (V)

$$NH_2—Y—R \quad (V)$$

wherein Y and R have meaning as defined hereinabove; or (b) reacting a compound of the formula VI $$Ar—COOH \quad (VI)$$

wherein Ar has meaning as defined hereinabove or a salt or reactive acid derivative thereof with a compound of the formula VII

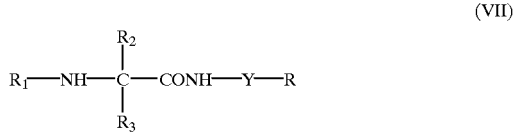

(VII)

wherein R, R$_1$, R$_2$, R$_3$, and Y have meaning as defined hereinabove; and, if required, protecting in each process any free functional groups (such as amino or carboxy) which are not participating in the reaction, and removing any such protecting groups and, if desired, converting a compound I obtainable according to the process or in another manner, in free form or in salt form, into another compound I, separating a mixture of isomers obtainable according to the process and isolating the desired isomer and/or converting a free compound I obtainable according to the process into a salt or converting a salt of a compound I obtainable according to the process into the free compound I or into another salt.

The reactions described above and below are carried out, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

In starting compounds and intermediates which are converted to the compounds of the invention in manner described herein, functional group present, such as thiol, carboxyl, amino and hydroxy groups, are optionally protected by conventional protecting groups that are common in preparative organic chemistry. Protected thio, carboxyl, amino and hydroxy groups are those that can be converted under mild conditions into free thiol, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Woots, "Protective Groups in Organic Synthesis", Wiley, N.Y. 1991, and also in "The Peptides", Vol. I, Schroeder and Luebke, Academic Press, London, N.Y., 1965.

A carboxy group is protected, for example, in the form of an ester group which can be removed selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or trisubstituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxy carbonyl, for example 1-methyl or 1-ethyl thioethoxycarbonyl, aroylmethoxycarbonyl wherein the aroyl group is benzoyl that is unsubstituted or substituted, for example, by halogen, such as bromine, for example phenacyl oxycarbonyl, 2-halo-lower alkoxycarbonyl, for example 2,2,2-trichloroethoxycarbonyl, 2-bromoethoxycarbonyl or 2-iodoethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonylgroup can also be substituted by two lower alkyl groups, for example methyl groups, and the amino group or the carboxy group of a second molecule of formula I. Compounds having such protecting groups can be prepared, for example, using dimethylchlorosilane as silylating agent.

A protected carboxy group is preferably lower alkoxycarbonyl, for example methoxy-, ethoxy- or tert-butoxy carbonyl, benzyloxycarbonyl, 4-nitrobenzyloxycarbonyl, 9-fluorenylmethoxycarbonyl or diphenylmethoxycarbonyl.

The removal of protecting groups that are not constituents of the desired end product of formulaI, for example the carboxy-protecting groups, is effected in a manner known per se, for example by means of solvolysis, especially hydrolysis, alcoholysis or acidolysis, or by means of reduction, especially hydrogenolysis or chemical reduction, as well as by photolysis, as appropriate stepwise or simultaneously, it being possible also to use enzymatic methods. The removal of the protecting groups is described, for example, in the standard works mentioned above in the section relating to "Protecting groups".

For example, protected carboxy, for example lower alkoxycarbonyl, tert-lower alkoxycarbonyl, lower alkoxy carbonyl substituted in the 2-position by a trisubstituted silyl group or in the 1-position by lower alkoxy or lower alkylthio, or unsubstituted or substituted diphenylmethoxy carbonyl can be converted into free carboxy by treatment with a suitable acid, such as formic acid, hydrogen chloride or trifluoroacetic acid, where appropriate with the addition of a nucleophilic compound, such as phenol or anisole. Carboxy can also be freed from lower alkoxycarbonyl by means of bases, such as hydroxides, for example alkali metal hydroxides, such as lithium hydroxide, sodium hydroxide or potassium hydroxide. Unsubstituted or substituted benzyloxy carbonyl can be freed, for example, by means of hydrogenolysis, i.e. by treatment with hydrogen in the presence of a metal hydrogenation catalyst, such as a palladium catalyst. Carboxy protected in the form of organic silyloxycarbonyl, such as tri-lower alkylsilyloxycarbonyl, for example trimethylsilyl oxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin.

The preparation of compounds of the invention according to process (a) involving the condensation of an amine of formula V with an acid of formula IV or a reactive functional derivative thereof is carried out using methodology well known for peptide synthesis.

The condensation according to process (a) of a substituted amine of formula V with a free carboxylic acid of formula IV is carried out advantageously in the presence of a condensing agent such as dicyclohexylcarbodiimide or N-(3-dimethylaminopropyl)-N'-ethylcarbodiimide and hydroxybenzotriazole, 1-hydroxy-7-azabenzotriazole or benzotriazol-1-yloxytris-(dimethylamino)phosphonium hexafluorophosphate (BOP Reagent), and triethylamine or N-methylmorpholine, in an inert polar solvent such as dimethylformamide or methylene chloride, preferably at room temperature.

The condensation of an amine of formula V with a reactive functional derivative of an acid of formula IV in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine, N-methylmorpholine or pyridine, preferably at room temperature.

Reactive functional derivatives of carboxylic acids of formula IV are preferably acid halides (e.g. the acid chloride) and mixed anhydrides, such as the pivaloyl or isobutyloxycarbonyl anhydride, or activated esters such as benzotriazole, 7-azabenzotriazole or hexafluorophenyl ester, or activated amides such as imidazolyl amides.

The amine starting material of formula V can be prepared according to methods described herein and illustrated in the examples.

The starting cyclic amino acids are either known or are prepared according to methods known in the art, e.g. by reaction of a ketone with e.g. sodium cyanide and ammonium carbonate to form the hydantoin and decomposition thereof with e.g. barium hydroxide.

The amino acid so obtained can be converted to other starting materials by first protecting the $NH_2$ group as e.g. a t-butoxycarbonyl (BOC) or benzyloxycarbonyl (CBZ) derivative, and then converting the carboxylic acid to a corresponding ester or amide by standard methodology. Conversion to starting materials wherein R is CONH—$SO_2$—$R_4$ is accomplished by first treating the BOC-protected amino acid with a condensing agent, e.g. 1-(3-dimethylaminopropyl)-3-ethyl-carbodiimide followed by a compound of the formula $R_4$—$SO_2$—$NH_2$ in the presence of a strong base, such as 1,8-diazabicyclo[5,4,0]undec-7-ene (DBU), in an inert solvent such as tetrahydrofuran.

The preparation of the compounds wherein R represents 5-tetrazolyl can be carried out according to procedures known in the art for the preparation of tetrazoles from nitriles e.g. as described in J. Am. Chem. Soc. 80, 3908 (1958), J. Org. Chem. 56, 2395 (1991) and U.S. Pat. No. 5,273,990.

Compounds of formula V wherein R represents cyano are prepared from the N-protected primary amides (which can in turn be prepared by treatment with e.g. phosphorus oxychloride in the presence of a base such as imidazole). Treatment of the nitrile with hydrazoic acid (preferably generated in situ) or a reactive azide derivative such as trialkylsilyl azide or trialkyltin azide yields the compound wherein R is 5-tetrazolyl.

If a trialkylsilyl azide (such trimethylsilyl azide) or a trialkyltin azide is used, the resulting tetrazole may be substituted by trialkyltin or trialkylsilyl. Such groups may be removed by hydrolysis, e.g. with dilute acid.

An N-protected tetrazole can also first be prepared from a suitably protected amide as described in U.S. Pat. No. 5,273,990.

Any resulting N-protected compound of formula V, e.g. the t-BOC or CBZ derivative is converted to the free amine according to methods well known in the art, e.g. by treatment with acid or by hydrogenolysis, respectively.

The starting materials of formula IV can be prepared by alkylation of a compound of formula IVa

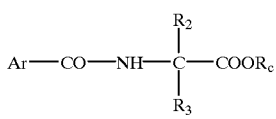

(IVa)

wherein Ar, $R_2$ and $R_3$ have meaning as defined hereinabove, and $R_c$ is an esterifying group, e.g. lower alkyl or benzyl, with an alkylating agent corresponding to $R_1$, e.g. methyl iodide, in the presence of a strong base, e.g. sodium hydride or DBU.

Alternately, the starting materials of formula IV can be prepared by acylation of an N-alkylated compound of formula VII below, e.g. wherein $R_1$ is lower alkyl, aryl-lower alkyl or cycloalkyl-lower alkyl.

The acylation to obtain starting materials of formula IV or IVa is carried out by condensation of an acid of the formula Ar—COOH (VI), or a functional reactive derivative thereof, with e.g. an amino acid ester of the formula VIII

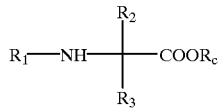

(VIII)

wherein $R_1$, $R_2$ and $R_3$ have meaning as defined herein, and $R_c$ is an esterifying group, e.g. lower alkyl or benzyl.

The acylation is carried out according to methods well-known in the art, e.g. by reacting an acyl halide of the acid of formula VI, e.g. the acid chloride, with an amino acid ester of formula VIII, in an inert solvent such as methylene chloride, in the presence of a base, such as an amine like triethylamine or pyridine.

The acylation of an acid of formula VI with an amino acid ester of formula VIII can also be carried out in the presence of a condensing agent such as N-(3-dimethylaminopropyl)-N'-ethylcarbodiimide as described hereinabove, optionally in the presence of e.g. hydroxybenzotriazole or 1-hydroxy-7-azabenzotriazole.

The amino acid esters and amino acids corresponding to acyl derivatives of formula IV and IVa are either known in the art or can be prepared according to methodology known in the art and illustrated in the examples.

Biarylalanines and/or derivatives thereof (wherein $R_3$ is biaryl-lower alkyl) can be prepared from aryl-alanine derivatives (wherein $R_3$ is aryl-lower alkyl) according to methods generally known in the art and illustrated in the examples.

For example, compounds wherein the biaryl group is 1-pyrrolylphenyl can be prepared from corresponding compounds wherein $R_3$ is aminophenyl-lower alkyl by treatment with e.g. 2,5-dimethoxytetrahydrofuran according to methodology known in pyrrole chemistry and illustrated in the examples. As a further example, compounds wherein the biaryl group is 3-thienylphenyl can be prepared from corresponding compounds wherein $R_3$ is e.g. (trifluoromethanesulfonyloxy)phenyl-lower alkyl by Pd catalyzed coupling with 3-thiophenboronic acid according to methodology described in J. Org. Chem. 57, 379 (1992).

Alternately, a biaryl-lower alkyl halide is first prepared and converted to the corresponding a-amino acid according to methods well known in the art. For example, 4-methylacetophenone is first converted to a 3-dialkylamino-p-tolylprop-2-ene-1-one by treatment with e.g. an N,N-dimethylformamide dialkyl acetal. Subsequent condensation with hydroxylamine-O-sulfonic acid yields 5-(4-tolyl)-isoxazole and treatment with, e.g. N-bromosuccinimide, yields 4-(5-isoxazolyl)-tolyl bromide which is converted to 3-[4-(5-isoxazolyl)phenyl]alanine and derivatives thereof as illustrated in the examples.

The condensation according to process (b) involving the condensation of an acid of formula VI with an amine of formula VII is carrried out as described above for the synthesis of intermediates of formula IV.

The intermediates of formula VII are essentially prepared as described for process (a), except that the group Ar—CO— in intermediates of formula IV is replaced by an N-protecting group such as benzyloxycarbonyl or t-butoxycarbonyl for condensation with intermediate of formula V, and said protecting group is subsequently removed.

A compound according to the invention which is obtainable by the process can be converted into another compound according to the invention in a manner known per se.

A compound according to the invention containing hydroxyl can be etherified by methods known per se. The etherification can be carried out, for example, using an alcohol, such as a substituted or unsubstituted lower alkanol, or a reactive ester thereof. Suitable reactive esters of the desired alcohols are, for example, those with strong inorganic or organic acids, such as corresponding halides, sulfates, lower alkanesulfonates or substituted or unsubstituted benzenesulfonates, for example chlorides, bromides, iodides, methane-, benzene- or p-toluenesulfonates. The etherification can be carried out, for example, in the presence of a base, an alkali metal hydride, hydroxide or carbonate, or of an amine. Conversely, corresponding ethers, such as lower alkoxy compounds, can be cleaved, for example, by means of strong acids, such as mineral acids, for example the hydrohalic acids hydrobromic or hydriodic acid, which may advantageously be present in the form of pyridinium halides, or by means of Lewis acids, for example halides of elements of main group III or the corresponding sub-groups. These reactions can be carried out, if necessary, with cooling or warming, for example in a temperature range from about −20° to about 100° C., in the presence or absence of a solvent or diluent, under inert gas and/or under pressure and, if appropriate, in a closed vessel.

Primary or secondary amino containing compounds of the formula I, their tautomers or salts can be N-alkylated in a manner known per se; likewise, carbamoyl or radicals containing carbamoyl can be N-alkylated. The (aryl) alkylation is carried out, for example, using a reactive ester of an (aryl)$C_1$–$C_7$alkyl halide, for example a bromide or iodide, (aryl)$C_1$–$C_7$alkylsulfonate, for example methanesulfonate or p-toluenesulfonate, or a di-$C_1$–$C_7$alkyl sulfate, for example dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrmethylammonium chloride, where, however, stronger basic condensing agents, such as alkali metal amides, hydrides or alkoxides, for example sodium amide, sodium hydride or sodium ethoxide, may be necessary. Amino can also be acylated in a manner known per se, for example analogously to variant a).

In compounds of the formula I which contain an esterified carboxyl group as a substituent, a group of this type can be converted into a free carboxyl group, for example by means of hydrolysis, for example in the presence of a basic agent, or of an acidic agent, such as a mineral acid. Tert-butyloxycarbonyl, for example, can furthermore be converted into carboxyl, for example in a manner known per se, such as treating with trihaloacetic acid, such as trifluoroacetic acid, and benzyloxycarbonyl can be converted into carboxyl, for example by catalytic hydrogenation in the presence of a hydrogenation catalyst, for example in the manner described below.

Depending on the procedure and reaction conditions, the compounds according to the invention having salt-forming properties can be obtained in free form or in the form of salts.

In view of the close relationship between the novel compound in the free form and in the form of its salts, in the preceding text and below the free compound or its salts may correspondingly and advantageously also be understood as meaning the corresponding salts or the free compound.

The novel compounds including their salts of salt-forming compounds can also be obtained in the form of their hydrates or can include other solvents used for crystallization.

Depending on the choice of the starting materials and procedures, the novel compounds can be present in the form of one of the possible isomers or as mixtures thereof, for example as pure optical isomers, such as antipodes, or as isomer mixtures, such as racemates.

Racemates obtained may be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic racemate with an optically active acid, such as a carboxylic acid, for example tartaric or malic acid, or sulfonic acid, for example camphorsulfonic acid, and separation of the diastereomeric salts obtained in this manner, for example on the basis of its differing solubilities, into the diastereomeric salts from which the desired enantiomer can be liberated by the action of suitable agents. The more active enantiomer is advantageously isolated.

The invention also relates to those embodiments of the process, according to which a compound obtainable as an intermediate in any step of the process is used as a starting material and the missing steps are carried out or a starting material in the form of a derivative or salt and/or its racemates or antipodes is used or, in particular, formed under the reaction conditions.

In the processes of the present invention, those starting materials are preferably used which lead to the compounds described as particularly useful. The invention likewise relates to novel starting materials which have been specifically developed for the preparation of the compounds according to the invention, to their use and to processes for their preparation.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration. The novel pharmaceutical preparations contain, for example, from about 10% to about 80%, preferably from about 20% to about 60%, of the active ingredient.

The pharmacologically active compounds of the invention can be used in the manufacture of pharmaceutical compositions that comprise an effective amount of the same on its own or in conjunction or admixture with excipients or carriers that are suitable for enteral or parenteral administration. Preferred are tablets and gelatin capsules that comprise the active constituent together with a) diluents, for example lactose, dextrose, sucrose, mannitol, sorbitol, cellulose and/or glycine, b) glidants, for example silica, talc, stearic acid, the magnesium or calcium salt thereof and/or polyethylene glycol, for tablets also c) binders, for example magnesium aluminum silicate, starch paste, gelatin, tragacanth, methylcellulose, sodium carboxymethylcellulose and/or polyvinylpyrrolidone, if desired d) dispersing or disintegrating agents, for example starches, agar, alginic acid or the sodium salt thereof, or foaming mixtures and/or e) absorbents, colouring agents, flavourings and sweeteners. Injectable preparations are preferably aqueous isotonic solutions or suspensions, and suppositories are advantageously produced from fatty emulsions or suspensions. These compositions may be sterilised and/or contain adjuvants, such as preservatives, stabilizers, wetting agents or emulsifiers, solubilisers, salts for regulating the osmotic pressure and/or buffers. In addition they may also contain other therapeutically valuable substances. These preparations are manufactured according to conventional mixing, granulating or coating methods and contain approximately from 0.1 to 100%, preferably approximately from 1 to 50%, of the active constituent. A unit dose for a mammal weighing approximately from 50 to 70 kg may contain between approximately 1 and 200 mg, of active ingredient.

The present invention also relates to methods of treatment with and methods of using the compounds of the invention and their pharmaceutically acceptable salts, or pharmaceutical compositions thereof, in mammals for inhibiting endothelin, and for the treatment of endothelin dependent conditions as described herein, e.g. cardiovascular disorders, such as hypertension, renal failure, myocardial isohemia, and bronchial disorders, such as asthma, in mammals.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviatrions used are those conventional in the art. The final compounds of the invention are isolated as either racemates or predominantly, as R-isomers (with respect to the asymmetric center bearing the $R_2$ substituent in formula I) depending on the starting materials and processes used. The compounds are preferably prepared starting from an amino acid having the D (or R) configuration at the asymmetric center bearing the $R_2$ and $R_3$ substituents in formula I. Products and intermediates obtained from starting materials having the R (or D) configuration may consist of a mixture of the R (or D) and S (or L) enantiomers due to some racemization in some of the synthetic steps involved.

EXAMPLE 1

A solution at 0° of N-3,5-dimethylbenzoyl-N-methyl-D-3-[4-(1-pyrrolyl)phenyl] alanine (1.06, 2.8 mmol) and 1-amino-1-cyclopropane N-(n-butanesulfonyl)carboxamide hydrochloride (1.04 g, 4.04 mmol) in 5 mL of DMF is treated with 1-(3-dimethylamino propyl)-3-ethylcarbodiimide hydrochloride (0.77 g, 4.04 mmol), 1-hydroxy-7-azabenzotriazole (0.55 g, 4.04 mmol), triethylamine (0.57 mL, 4.04 mmol), stirred 2 hours at 0° C. followed by stirring at room temperature overnight. The mixture is poured onto 1N HCl in ice and extracted with EtOAc (2x). The organic layer is washed with 1N HCl, water, brine, dried over $MgSO_4$, filtered and concentrated. Chromatography on silica gel with ethyl acetate gives Ⓡ-N-[N-3,5-dimethylbenzoyl-N-methyl-3-[4-(1-pyrrolyl)phenyl]alanyl]-1-aminocyclo propane-1-N-(n-butanesulfonyl)carboxamide as a white solid melting at 150–155° C. The structure is as follows:

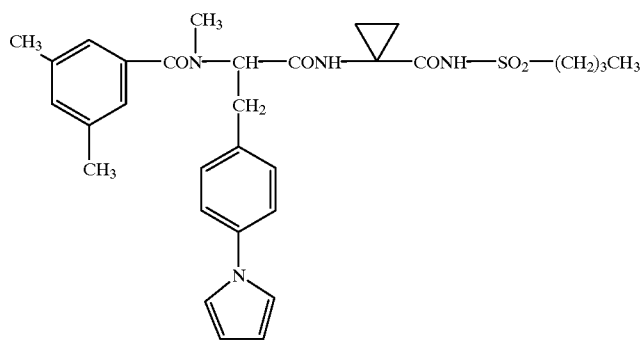

One starting material can be obtained as follows:

A solution of 4-nitro-D-phenylalanine (25 g) in 300 mL of methanol is treated with dry hydrogen chloride gas for 10 minutes. The solution is stirred at room temperature overnight. The suspension is concentrated and triturated with 300 mL of ether. The solid is collected and dried to give 4-nitro-D-phenylalanine methyl ester hydrochloride. To a solution of 4-nitro-D-phenylalanine methyl ester hydrochloride (25 g, 96 mmol) in 500 mL of methylene chloride at 0° C. is added 3,5-dimethylbenzoyl chloride (19.3 g, 110 mmol) and triethylamine (29.4 mL, 211 mmol) in 100 mL of methylene chloride. The reaction mixture is warmed to room temperature and stirred overnight. The mixture is concentrated, 100 mL of ethyl acetate is added and the substance is passed through a pad of silica gel. The filtrate is concentrated and the residue is recrystallized from (1:1) toluene/heptane to give N-(3,5-dimethylbenzoyl)-4-nitro-D-phenylalanine methyl ester. To a solution of N-(3,5-dimethylbenzoyl)-4-nitro-D-phenylalanine methyl ester (35 g, 98 mmol) and methyl iodide (18.7 mL, 0.3 mol) in 600 mL of DMF is added in portions sodium hydride (4.2 g, 100 mmol, 60% dispersion) at 0° C. The reaction is warmed to room temperature and stirred overnight. The reaction mixture is poured into 1500 mL of ethyl acetate and washed with water, brine, dried over $MgSO_4$ and concentrated. Chromatography on silica gel with a gradient solvent system: methylene chloride, followed by 10% ethyl acetate/methylene chloride, followed by 20% ethyl acetate/methylene chloride gives the white solid N-(3,5-dimethylbenzoyl)-N-methyl-D-4-nitrophenylalanine methyl ester. A solution of N-(3,5-dimethylbenzoyl)-N-methyl-D-4-nitrophenylalanine methyl ester (5.0 g, 13.5 mmol) in 50 mL of methanol and 100 mL of ethyl acetate is added 1.6 g of 10% Pd/C. The suspension is hydrogenated at 50 psi overnight. The mixture is filtered and concentrated to give the crude amine. The amine is used as is without further purification. The above crude product of N-(3,5-dimethylbenzoyl)-N-methyl-D-4-aminophenylalanine methyl ester (5.15 g, 15.2 mmol) is dissolved in 150 mL of acetic acid. 2,5-Dimethoxytetrahydrofuran is added and the mixture is heated to 90° C. for 1 hour, then cooled and poured into ethyl acetate. The organic layer is washed with 1N HCl, H$_2$O, sat. NaHCO$_3$, brine, dried over MgSO$_4$ and concentrated. Chromatography on silica gel with 1:2 ethyl acetate/hexane gives N-(3,5-dimethylbenzoyl)-N-methyl-D-4-(1-pyrrolyl)-phenylalanine methyl ester. To a solution of N-(3,5-dimethylbenzoyl)-N-methyl-4-(1-pyrrolyl)-phenylalanine methyl ester (3.3 g, 8.5 mmol) in 50 mL of methanol/THF (1:1) at room temperature is added 1N lithium hydroxide (10.14 ml, 10.1 mmol). The reaction is stirred overnight. The mixture is concentrated and washed with ether. The residue is acidified with 1N HCl and extracted with ethyl acetate, washed with H$_2$O, brine, dried (MgSO$_4$), filtered and concentrated giving N-(3,5-dimethylbenzoyl)-N-methyl-D-4-(1-pyrrolyl)-phenylalanine.

The other starting material can be obtained as follows:

To a solution of 1-amino-1-cyclopropanecarboxylic acid (1.0 g, 10 mmol) in 80 mL of dioxane is added 1N NaOH (10 mL, 10 mmol) and di-t-butyldicarbonate (2.18 g, 10 mmol). The reaction mixture is stirred overnight, then concentrated. The residue is dissolved in water and washed with ethyl acetate. The aqueous layer is acidified with 1N HCl, saturated with NaCl and extracted with ethyl acetate. The organic layer is evaporated to dryness giving N-t-butoxycarbonyl-1-aminocyclopropane-1-carboxylic acid. To a solution of 1,1'-carbonyldiimidazole (1.62 g) in 20 mL of THF is added N-t-butoxycarbonyl-1-amino-1-cyclopropane carboxylic acid (91.71 g, 10 mmol) in 20 mL of THF. The mixture is stirred for 30 minutes, then refluxed 30 minutes. The reaction is cooled to room temperature. N-n-Butane sulfonylamide and 1,8-diazabicyclo [5.4.0] undec-7-ene (1.5 mL, 10 mmol) in 5 mL of THF are added. The mixture is stirred at room temperature overnight, and poured into 1N HCl. The product is extracted with ethyl acetate. The organic layer is washed with brine, dried over MgSO$_4$ and concentrated. The residue is triturated with ether giving 1-(t-butoxycarbonylamino)-cyclopropane-1-N-(n-butyl sulfonyl)carboxamide. Treatment with acid under standard conditions to remove the N-t-butoxycarbonyl group yields 1-aminocyclopropane-1-N-(n-butanesulfonyl) carboxamide hydrochloride.

EXAMPLE 2

Prepared similarly to example 1 are the following compounds of the formula III (Ar=2,4-dimethylphenyl):

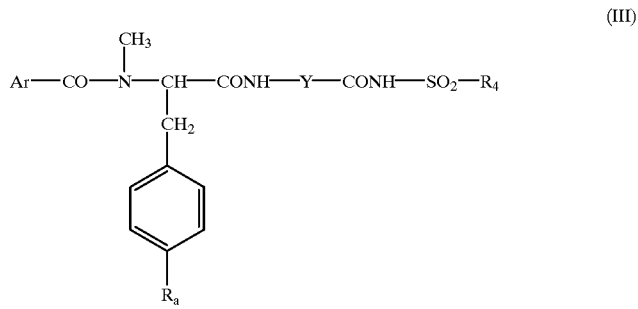

(III)

| Compound | R$_a$ | Y | R$_4$ | m.p. (° C.) | Salt |
|---|---|---|---|---|---|
| 2 a) | 1-pyrrolyl | cyclopentylidenyl | phenyl | 152–155° | Na |
| 2 b) | 5-isoxazolyl | cyclopentylidenyl | methyl | 148–155° | Na |
| 2 c) | 5-isoxazolyl | cyclopentylidenyl | n-butyl | 132–138° | Na |
| 2 d) | 5-isoxazolyl | cyclopentylidenyl | 3,4-methylenedioxyphenyl | 160–167° | Na |
| 2 e) | 5-isoxazolyl | cyclopentylidenyl | 2-methylphenyl | 167–170° | Na |
| 2 f) | 5-isoxazolyl | 2-indanylidenyl | phenyl | 178–185° | Na |
| 2 g) | 1-pyrrolyl | 2-indanylidenyl | n-butyl | 132–140° | |
| 2 h) | 5-isoxazolyl | cyclopropylidenyl | phenyl | 120–123° | |
| 2 i) | 1-pyrrolyl | cyclopentylidenyl | n-butyl | 65–68° | |
| 2 j) | 1-pyrrolyl | cyclopropylidenyl | n-butyl | 187–190° | |
| 2 k) | 1-pyrrolyl | cyclopentylidenyl | cyclopentyl | 170–172° | Na |
| 2 l) | pyrrolidino | cyclopentylidenyl | n-butyl | 75–78° | |
| 2 m) | N(CH$_3$)$_2$ | cyclopentylidenyl | n-butyl | 60–63° | |
| 2 n) | 1-pyrrolyl | cyclopropylidenyl | 4-carboxy-n-butyl | 138–144° | |
| 2 o) | 3-thienyl | cyclopropylidenyl | n-butyl | 155° dec. | |
| 2 p) | 3-thienyl | 4-tetrahydro-4-H-pyranylidenyl | n-butyl | 152–156° | |
| 2 q) | pyrrolidino | 4-tetrahydro-4-H-pyranylidenyl | n-butyl | 97–100° | |
| 2 r) | 3-thienyl | cyclopentylidenyl | n-butyl | 100° dec. | |
| 2 s) | 3-thienyl | 2-indanylidenyl | n-butyl | 145–150° | |
| 2 t) | 1-pyrrolyl | cyclopentylidenyl | (CH$_2$)CO$_2$CH$_3$ | 195–198° | |
| 2 u) | 1-pyrrolyl | cyclopropylidenyl | (CH$_2$)COOH | 205–210° | |
| 2 v) | phenyl | cyclopentylidenyl | phenyl | 96–100° | |
| 2 w) | 5-isoxazolyl | cyclopentylidenyl | phenyl | 172–176° | |
| 2 x) | 5-isoxazolyl | cyclopentylidenyl | benzyl | 152–154° | |
| 2 y) | 5-isoxazolyl | cyclohexylidenyl | phenyl | 170–179° | |
| 2 z) | 5-isoxazolyl | 2-propylidenyl | n-butyl | 130–137° | Na |
| 2 aa) | 1-pyrrolyl | 4-tetrahydro-4-H- | n-butyl | 114–116° | |

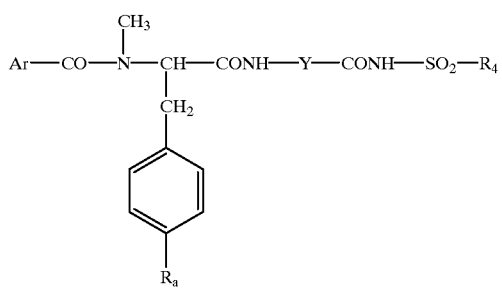

(III)

| Compound | $R_a$ | Y | $R_4$ | m.p. (° C.) | Salt |
|---|---|---|---|---|---|
| 2 bb) | 1-pyrrolyl | pyranylidenyl 4-tetrahydro-4-H-thiopyranylidenyl | n-butyl | 138–143° | |
| 2 cc) | 1-pyrrolyl | 4-tetrahydro-S-di-oxo-4-H-thio-pyranylidenyl | n-butyl | 213–217° | |
| 2 dd) | 1-pyrrolyl | 4-tetrahydro-S-oxo-4-H-thio-pyranylidenyl | n-butyl | 212–215° | |
| 2 ee) | 2-pyridyl | cyclopentylidenyl | n-butyl | 80–82 | |
| 2 ff) | 2-pyridyl | 4-tetrahydro-4-H-pyranylidenyl | n-butyl | 87–91 | |
| 2 gg) | 1-pyrrolyl | 4-ethylenedioxy-cyclohexylidenyl | n-butyl | 74–76° | |
| 2 hh) | 5-isoxazolyl | cyclopropylidenyl | n-butyl | 172–175° | |

The compound of example 2 bb) can be converted to the compound of example 2 dd) as follows:

A solution of the sulfide (600 mg, 0.94 mmole) in 50 mL of 1:1 EtOAc/EtOH is treated with 30% aqueous hydrogen peroxide (5 mL, 44.0 mmoles) at room temperature. The solution is stirred at 50° C. for 15 minutes. The reaction mixture is diluted with 500 mL 1:1 ethyl acetate/ether, washed with three portions of water (600 mL), washed once with 100 mL brine, dried over magnesium sulfate, and concentrated in vacuo to give the crude product. Chromatography on silica using methanol in ethyl acetate (0 to 20%) gives the sulfoxide as a mixture of diastereomers. The product is recrystallized from toluene to give sulfoxide 2(dd) as a single diastereomer.

The preparation of various amino acid starting materials and derivatives is described in examples 5 and 6.

EXAMPLE 3

Similarly to the prior examples are prepared the following compounds of the formula III, wherein $R_a$ represents 1-pyrrolyl and $R_4$ represents n-butyl

| Compound | Ar | Y | m. p. (° C.) |
|---|---|---|---|
| 3 a) | 4-methoxyphenyl | cyclopentylidenyl | 87–94° |
| 3 b) | 3,5-dimethoxyphenyl | cyclopentylidenyl | 71–79° |
| 3 c) | 3-hydroxy-5-methyl-phenyll | cyclopentylidenyl | |
| 3 d) | 4-pyridyl | cyclopentylidenyl | 108–110° |
| 3 e) | 5-methyl-2-pyridyl | cyclopentylidenyl | |
| 3 f) | 4-ethoxyphenyl | 2-indanylidenyl | 177–179° |
| 3 g) | 3,5-dimethoxyphenyl | 2-indanylidenyl | 87–89° |

EXAMPLE 4

(a) Similarly to procedure described in example 1, condensation of N-(3,5-dimethylbenzoyl)-N-methyl-D-4-(1-pyrrolyl)-phenylalanine with methyl 4-amino-4-tetrahydropyrancarboxylate yields methyl (R)-N-[N-(3,5-dimethylbenzoyl)-N-methyl3-[4-(1-pyrrolyl) phenyl]alanyl]-4-amino-4-tetrahydropyrancarboxylate, m.p. 124–126°.

(b) The above ester (340 mg, 0.65 mmol) is dissolved in 10 mL (1:1) methanol/THF. Lithium hydroxide (1 M, 5 mL, 5 mmol) is added and the mixture stirred for 1 hour at room temperature. Hexane (100 mL) is added and the carboxylic acid is extracted with 0.1 M NaOH. The basic layer is acidified with 1 N HCl and extracted with ether and ethyl acetate. The organic layer is washed with brine, dried over MgSO₄, filtered and concentrated. The oil is triturated with ether/pentane (1:1), the solid collected and dried under high vacuum at 60° C., to yield (R)-N-[N-(3,5-dimethylbenzoyl)-N-methyl-3-[4-(1-pyrrolyl) phenyl]alanyl]-4-amino-4-tetrahydropyrancarboxylic acid, m.p. 115–118°.

(c) Similarly prepared is (R)-N-[N-(3,5-dimethylbenzoyl)-N-methyl-3-[4-(1-pyrrolyl) phenyl]alanyl]-1-aminocyclopropane-1-carboxylic acid, m.p. 212–214° C.

(d) Similarly prepared is (R)-N-[N-(3,5-dimethylbenzoyl)-N-methyl-3-[4-(1-pyrrolyl) phenyl]alanyl]-1-amino-4-ethylenedioxycyclohexane-1-carboxylic acid, m.p. 130–135° C.

EXAMPLE 5

The starting amino acids bearing the $R_3$ substituent (in formula I) and derivatives can be prepared according to methods known in the art and illustrated below.

(a) To a solution of N-t-butoxycarbonyl-D-tyrosine methyl ester (2.5 g, 9.48 mmol) in 10 mL of methylene chloride and pyridine (1.9 mL, 23.7 mmol) at −15° C. is added triflic anhydride (1.9 mL, 11.4 mmol). The reaction is stirred 30 minutes. The mixture is washed with water, 0.5 N NaOH, 15% aqueous citric acid, brine dried over $MgSO_4$, filtered and concentrated giving N-t-butoxycarbonyl-4-trifluoromethanesulfonyloxy-D-phenyl alanine methyl ester. A solution of 3-thiopheneboronic acid (1.4 g, 10.9 mmol), potassium carbonate (1.13 g, 8.2 mmol) in 25 mL of toluene is heated to 80° C. and the catalyst tetrakis (triphenyl phosphine)-Pd (0.19 g, 0.16 mmol) is added. N-t-Butoxycarbonyl-4-trifluoro methanesulfonyloxy-D-phenylalanine methyl ester (2.34 g, 5.47 mmol) in 25 mL of toluene is added dropwise and stirred at 80° C. for 3 hours. The mixture is filtered through Celite and washed with ethyl acetate. The organic layer is washed with 0.5 N NaOH (2×), 15% citric acid, water, brine, dried over $MgSO_4$, filtered and concentrated. Chromatography on silica gel with ethyl acetate/toluene (1:5) gives N-t-butoxy carbonyl-4-(3-thienyl)-D-phenylalanine methyl ester. Treatment of the above with dilute HCl in 1,4-dioxane at room temperature overnight yields 4-(3-thienyl)-D-phenylalanine methyl ester hydrochloride.

(b) A suspension of 2-(4-methylphenyl)pyridine (3.9 g, 23.0 mmol), N-bromo-succinimide (4.3 g, 24.0 mmol) and benzoyl peroxide (0.20 g, 0.83 mmol) in dry carbon tetrachloride (100 mL) is refluxed for 4 hours. After cooling to room temperature, additional benzoyl peroxide (0.15 g, 0.82 mmol) is added. The reaction mixture is refluxed for 13 hours. After cooling to room temperature, the mixture is filtered and concentrated in vacuo, giving 2-[(4-bromomethyl)phenyl]-pyridine as an orange oil.

A solution of N-(diphenylmethylene)glycine ter-butyl ester (6.75 g, 22.9 mmol) and 2-[(4-bromomethyl)phenyl] pyridine (5.71 g, 23.0 mmol) in dry dichloromethane (40 mL) is added via an addition funnel to a suspension of N-benzylcinchoninium chloride (1.42 g, 3.4 mmol) and sodium hydroxide (13.4 g, 335.0 mmol) in water (40 mL). The resulting dark red mixture is stirred at room temperature overnight. The reaction mixture is diluted with brine (100 mL) and extracted with 2 portions of dichloromethane (50 mL). The organic layer is dried over magnesium sulfate, filtered and concentrated in vacuo. Chromatography on silica with ethyl acetate/dichloromethane 5:95 gives 2-[4-a-(N-diphenylmethylene)aminopropanoic acid tert-butyl ester)phenyl]pyridine as an orange oil. p-Toluenesulfonic acid monohydrate (2.18 g, 11.5 mmol) is added in one portion to a solution of 2-[4-a-(N-diphenylmethylene) aminopropanoic acid tert-butyl ester)phenyl]pyridine (4.71 g, 10.0 mmol) in a mixture of acetonitrile (175 mL) and water (17.5 mL). The mixture is stirred at room temperature overnight. The solution is diluted with ethyl ether (200 mL) and extracted with 2 portions of 1N hydrochloric acid (100 mL). The aqueous layer is basified to pH=11 with 40% aqueous potassium hydroxide and extracted with 2 portions of dichloromethane (100 mL). The organic layer is dried over sodium sulfate, filtered and concentrated in vacuo to give 2-[(4-a-aminopropanoic acid tert-butyl ester)phenyl] pyridine as an orange oil.

(c) A solution of sodium methoxide in methanol is generated by dissolving sodium metal (0.89 g, 30.0 mmol) in dry methanol (25 mL). This solution is added via an addition funnel to a solution of benzamidine hydrochloride hydrate (2.35 g, 15.0 mmol) and 3-dimethyl-amino-2-methylpropenal (1.16 g, 10.2 mmol) in dry methanol (50 mL) at room temperature. The reaction mixture is refluxed for 4 hours, then cooled at room temperature. The mixture is concentrated in vacuo and the residue partitioned between dichloromethane (50 mL) and water (50 mL). The aqueous layer is extracted with dichloromethane (50 mL) and the combined organic layers are dried over magnesium sulfate. Filtration and concentration in vacuo gives 5-methyl-2-phenyl-pyrimidine as a yellow solid.

A suspension of 5-methyl-2-phenyl-pyrimidine (3.0 g, 17.6 mmol), N-bromosuccinimide (2.0 g, 11.2 mmol) and a,a'-azobis(isobutyronitrile) (0.10 g, 0.61 mmol) in dry carbon tetrachloride (150 mL) is refluxed for 0.5 hours. After cooling to room temperature, the mixture is filtered and the filtrate is concentrated in vacuo, giving 5-bromomethyl-2-phenyl-pyrimidine as an orange oil.

A solution of N-(diphenylmethylene)glycine tert-butyl ester (3.2 g, 10.8 mmol) and 5-bromomethyl-2-phenyl-pyrimidine (2.8 g, 11.2 mmol) in dry dichloromethane (25 mL) is added via an addition funnel to a suspension of N-benzylcinchoninium chloride (0.71 g, 1.7 mmol) and sodium hydroxide (6.7 g, 167.5 mmol) in water (20 mL). The resulting dark red mixture is stirred at room temperature for 2 days. The reaction mixture is diluted with brine (100 mL) and extracted with 2 portions of dichloromethane (100 mL). The organic layer is dried over magneiusm sulfate, filtered and concentrated in vacuo. Chromatography on silica with ethyl acetate/dichloromethane 5:95 gives 5-[a-(N-diphenylmethylene)aminopropanoic acid tert-butyl ester]-2-phenyl-pyrimidine as a yellow oil.

p-Toluenesulfonic acid monohydrate (0.72 g, 3.8 mmol) is added in one portion to a solution of 5-[a-(N-diphenylmethylene)aminopropanoic acid tert-butyl ester]-2-phenyl-pyrimidine (1.2 g, 2.6 mmol) in a mixture of acetonitrile (50 mL) and water (5 mL). The mixture is stirred at room temperature overnight. The solution is diluted with ethyl ether (100 mL) and extracted with 2 portions of 1N hydrochloric acid (50 mL). The aqueous layer is basified to pH=12 with 40% aqueous potassium hydroxide and extracted with 2 portions of dichloromethane (50 mL). The organic layer is dried over sodium sulfate, filtered and concentrated in vacuo to give 5-(a-aminopropanoic acid tert-butyl ester)-2-phenyl-pyrimidine as a yellow oil.

(d) A solution of thionyl chloride (6.5 ml) in dry methanol (280 ml) at −20° C. is treated with (D)-3-(biphenyl-4-yl)-alanine (3.7 g, 13.3 mmol) (Y. Yabe et al., Chem. Pharm. Bull. 24(12), 3149 (1976)). The reaction mixture is refluxed overnight and concentrated in vacuo. Recrystallization from methanol/ether gives (D)-3-(biphenyl-4-yl)-alanine methyl ester hydrochloride; $[a]_D$=+13°(c=1.025, methanol).

A solution of (D)-3-(biphenyl-4-yl)-alanine methyl ester hydrochloride (315 mg, 0.94 mmol) in dry tetrahydrofuran (0.4 ml) is treated at room temperature with water (0.4 ml), formalin (0.15 ml, 1.88 mmol) and freshly distilled cyclopentadiene (0.3 ml, 3.63 mmol). The slightly yellow solution is stirred at room temperature for 2 hours, washed with hexane (100 ml), diluted with 4% sodium bicarbonate solution (100 ml) and extracted with chloroform (200 ml). The organic layer is dried over magnesium sulfate, filtered and concentrated in vacuo to give a bicyclic intermediate. This material is dissolved at room temperature under nitrogen atmosphere in chloroform (4.7 ml) and treated with trifluoroacetic acid (4.7 ml) and triethylsilane (0.45 ml). The solution is stirred for 20 hours and concentrated in vacuo. The crude product is dissolved in ethyl acetate (200 ml) and washed with 1 M hydrochloric acid (100 ml) and saturated sodium bicarbonate solution (100 ml). The organic layer is dried over magnesium sulfate, filtered and concentrated in vacuo to give N-methyl-(D)-3-(biphenyl-4-yl)-alanine methyl ester as a white foam.

A solution of N-methyl-(D)-3-(biphenyl-4-yl)-alanine methyl ester in chloroform (5 ml) is treated with 2 M sodium carbonate (0.6 ml) and 3,5-dimethylbenzoyl chloride (0.3 ml, 1.4 mmol). The reaction mixture is stirred at room temperature for 2.5 hours, diluted with ethyl acetate (200 ml) and washed with 4% sodium bicarbonate solution (100 ml), water (100 ml), 1 M hydrochloric acid (100 ml) and again water (100 ml). The organic layer is dried over magnesium sulfate, filtered and concentrated in vacuo. Chromatography on silica with ethyl acetate/hexane 4:1 gives N-(3,5-dimethylbenzoyl)-N-methyl-(D)-3-(biphenyl-4-yl)-alanine methyl ester; [a]$_D$=+48°(c=0.685, methanol); ee >98% (HPLC: Chiralcel OF). N-(3,5-Dimethylbenzoyl)-N-methyl-(D)-3-(biphenyl-4-yl)-alanine methyl ester (110 mg, 0.27 mmol) is hydrolyzed at 0° C. with lithium hydroxide (13 mg, 0.31 mmol) in MeOH (0.8 ml), water (0.4 ml) and tetrahydrofuran (0.4 ml). After 2 hours the reaction mixture is diluted with ether (200 ml) and washed with three portions of water (100 ml). The combined aqueous layers are acidified to pH=2 with 1 M hydrochloric acid and extracted with two portions of ethyl acetate (200 ml). The ethyl acetate extracts are dried over magnesium sulfate, filtered and concentrated in vacuo to give N-(3,5-dimethylbenzoyl)-N-methyl-(D)-3-(biphenyl-4-yl)-alanine as a white foam; [a]$_D$=+7.5°(c=1.0, methanol).

(e) N-(3,5-Dimethylbenzoyl)-N-methyl-(D,L)-3-[4-(3-thienyl)-phenyl]-alanine is synthesized from (D,L)-3-[4-(3-thienyl)phenyl]-alanine ethyl ester by coupling with 3,5-dimethylbenzoic acid and subsequent methylation (NaH, MeI, N,N-dimethylformamide).

(D,L)-3-[4-(3-Thienyl)phenyl]alanine ethyl ester is synthesized by alkylation of N-(diphenylmethylene)glycine ethyl ester with 4-(3-thienyl)benzyl bromide (Lit. G. D. Hartmann et al., *J. Org. Chem.*, 51, 142–148 (1986)) in a biphasic system (aqueous sodium hydroxide/dichloromethane) in the presence of a phase transfer catalyst (tetrabutylammonium hydrogensulfate) and subsequent removal of the protecting group (p-toluenesulfonic acid, water, acetonitrile).

(f) 4-Methylacetophenone (100 g) and N,N-dimethylformamide diethylacetal (200 ml) are heated on reflux under nitrogen athmosphere for 20 hours to give, after evaporation, crude 3-dimethylamino-1-p-tolylprop-2-ene-1-one. *J. Org. Chem.*, 45, 4857–60 (1980)

At 0° C. a solution of hydroxylamine-O-sulfonic acid (93 g) in dry methanol (700 ml) is added over 2 minutes to a solution of crude 3-dimethylamino-1-p-tolylprop-2-ene-1-one (148 g) in dry methanol (1 l). The mixture is stirred at ambient temperature for 20 minutes, then carefully poured into a solution of sodium bicarbonate (150 g) in water (11 l). After standing at room temperature overnight (for convenience) the precipitate is collected and dried to give crude 5-(4-methylphenyl)-isoxazole. In order to obtain purer product, the material can be purified by flash chromatography on silica gel, using hexane/ethyl acetate (4:1) as eluent. To a solution of 5-(4-methylphenyl)-isoxazole (17 g) and N-bromosuccinimide (19 g) in tetrachloromethane (500 ml) under nitrogen, bisbenzoyl peroxide (0.43 g) is added, and the mixture heated on reflux overnight. The solvent is evaporated, and the residue purified by flash chromatography (silica gel, hexane/ethyl acetate 4:1) to give pure 5-(4-bromomethylphenyl)-isoxazole.

5-(4-bromomethylphenyl)-isoxazole (700 mg) is dissolved in dichloromethane (20 ml) and stirred vigorously with a solution of tetrabutylammonium hydrogen-sulfate in 2.5 molar aqueous sodium hydroxide, at room temperature, overnight. The organic layer is then separated off and concentrated. The residue is partitioned between ether and water, the ether phase washed with water and brine, dried over magnesium sulfate and evaporated to give crude N-diphenyl methylene-3-[4-(5-isoxazoly)-phenyl]-alanine ethyl ester.

Crude (±)-N-diphenyl methylene-3-[4-(5-isoxazolyl)-phenyl]-alanine ethyl ester (280 mg) was treated with p-toluenesulfonic acid monohydrate (100 mg) in acetonitrile (35 ml) and water (3.5 ml) at ambient temperature for 3.5 hours. After concentration the residue is extracted with ether and 1N sodium hydroxide, washed with brine, dried, and concentrated to give crude 3-[4-(5-isoxazolyl)-phenyl]-alanine ethyl ester.

Crude 3-[4-(5-isoxazolyl)-phenyl]-alanine ethyl ester (660 mg) is dissolved in chloroform (6.6 ml), stirred vigorously with 2N aqueous sodium carbonate (1.4 ml), and after cooling to 10° C., 3,5-dimethylbenzoylchloride (0.7 ml) is added. Stirring is continued for 1 hour at 10° C. and for 2 hours at ambient temperature. Then extraction with di chloromethane/water, washing with 10% aqueous citric acid, and with brine, followed by evaporation gives the crude product. Flash chromatography on silica gel, hexane/ethyl acetate (4:1), gives pure N-(3,5-dimethylbenzoyl)-3-[4-(5-isoxazolyl)-phenyl]-alanine ethyl ester.

A solution of N-(3,5-dimethylbenzoyl)-3-[4-(5-isoxazolyl)-phenyl]-alanine ethyl ester (3.8 g) and methyliodide (1.8 ml) in dry N,N-dimethylformamide (40 ml) is cooled in an ice bath and sodium hydride (60% in oil, 390 mg) is added in portions. The mixture is allowed to warm to room temperature during 5 hours, then poured into water, extracted with ethyl acetate, the organic phase washed with water, and with brine, dried and evaporated. Flash chromatography of the residue on silica gel (hexanelethyl acetate 3:1) gives pure N-(3,5-di methylbenzoyl)-N-methyl-3-[4-5-isoxazolyl)-phenyl]-alanine ethyl ester. N-(3,5-dimethylbenzoyl)-N-methyl-3-[4-(5-isoxazolyl)-phenyl]-alanine ethyl ester (44 mg) is treated with lithium hydroxide monohydrate (5 mg) in methanol (0.5 ml), tetrahydrofurane (0.25 ml), and water (0.25 ml) for 3 hours at room temperature. The mixture is then partitioned between water and ether, the water phase acidified with 1N hydrochloric acid, and subsequently extracted with ethyl acetate. The ethyl acetate phase is washed with brine, dried, and evaporated to give N-(3,5-dimethylbenzoyl)-N-methyl-3-[4-(5-isoxazolyl)-phenyl]-alanine.

(g) A mixture of 3,5-dimethylbenzamide (22.6 g, 0.15 mol) and glyoxylic acid monohydrate (15.3 g, 0.17 mol) in acetone (120 ml) is heated under nitrogen atmosphere at reflux for 6 h. The solvent is evaporated in vacuo to give 2-hydroxy-N-(3,5-dimethylbenzoyl)glycine. To a solution of 2-hydroxy-N-(3,5-dimethylbenzoyl)glycine in methanol (350 ml) is added concentrated sulfuric acid (4.6 ml) at room temperature. The mixture is stirred for 2 days and then concentrated in vacuo. The residue is diluted with ethyl acetate, washed with two portions of saturated sodium bicarbonate solution and with two portions of brine. The organic layer is dried over magnesium sulfate and concentrated in vacuo to give 2-methoxy-N-(3,5-dimethyl benzoyl) glycine methyl ester.

To a solution of 2-methoxy-N-(3,5-dimethylbenzoyl) glycine methyl ester (16.7 g, 66.5 mmol) in toluene (70 ml) under nitrogen atmosphere is added phosphorus thrichloride (6.0 ml, 68.7 mmol) at room temperature. The reaction mixture is heated at 70° C. for 16 h. Then, trimethyl phosphite (8.1 ml, 68.7 mmol) is added dropwise to the stirred mixture at 70° C. and stirring is continued for further 2 h at 70° C. The solvent is evaporated in vacuo. The residue is diluted with hexane, filtered, and washed with ethyl acetate. The combined filtrate is concentrated in vacuo and the crude material is purified by column chromatography on silica with ethyl acetate to give trimethyl 2-(3,5-dimethylbenzoyl)amino-phosphonoacetate. A mixture of 1,2,4-triazole (4.06 g, 58.7 mmol), potassium carbonate (9.05 g, 65.5 mmol), 4-fluorobenzaldehyde (6.3 ml, 58.7 mmol), and copper(I) oxide (0.26 g, 1.82 mmol) in pyridine (30 ml) is heated under nitrogen atmosphere at reflux overnight. After pyridine is distilled, the residue is diluted with chloroform, filtered, and washed with chloroform. The combined filtrate is washed with water, dried over magnesium sulfate, and concentrated in vacuo. The crude material is purified by column chromatography on silica with hexane/ethyl acetate (1:2) to give 4-(1,2,4-triazol-1-yl)-benzaldehyde and with ethyl acetate/methanol (19:1) to give 4-(1,3,4-triazol-1-yl)-benzaldehyde.

To a solution of trimethyl 2-(3,5-dimethylbenzoyl) amino-phosphonoacetate (0.51 g, 1.54 mmol) in methylene chloride (3.0 ml) under nitrogen atmosphere is added 1,8-diazabyclo[5.4.0]undec-7-ene (0.24 ml, 1.60 mmol). After 10 minutes, 4-(1,2,4-triazol-1-yl)-benzaldehyde (0.27 g, 1.57 mmol) is added and stirring is continued for 3 h. The reaction mixture is diluted with diethyl ether. The prepicipates are filtered, washed with diethyl ether and water successively, and dried in vacuo to give methyl 2-(3,5-dimethylbenzoyl)amino-3-[4-(1,2,4-triazol-1-yl) phenyl]acrylate.

To a cooled (0° C.) solution of methyl 2-(3,5-dimethyl benzoyl) amino-3-[4-(1,2,4-triazol-1-yl)-phenyl]-acrylate (0.35 g, 0.94 mmol) and iodomethane (0.20 ml, 3.21 mmol) in N,N'-dimethylformamide (3.0 ml) under nitrogen atmosphere is added sodium hydride (0.045 g, 60% in oil, 1.12 mmol). After 1 hour, the mixture is warmed to room temperature and stirred for 1 hour. The mixture is diluted with diethyl ether and washed with water and with brine. The organic layer is dried over magnesium sulfate and concentrated in vacuo to give methyl 2-[N-(3,5-dimethylbenzoyl)-N-methyl]amino-3-[4-(1,2,4-triazol-1-yl) phenyl]acrylate. A solution of 2-[N-(3,5-dimethylbenzoyl)-N-methyl]amino-3-[4-(1,2,4-triazol-1-yl)-phenyl]acrylate (1.50 g, 4.5 mmol) in methanol (50 ml) is hydrogenated over platinum oxide (1 mg) under 3atm hydrogen atmosphere overnight. Catalyst is removed by fitiration and the filtrate is concentrated in vacuo. The crude material is purified by column chromatography on silica with hexane/ethyl acetate (1:5) to give N-(3,5-dimethylbenzoyl)-N-methyl-3-[4-(1,2,4-triazol-1-yl)-phenyl]-(D,L)-alanine methyl ester.

N-(3,5-dimethylbenzoyl)-N-methyl-3-[4-(1,2,4-triazol-1-yl)-phenyl]-(D,L)-alanine methyl ester (1,24 g, 3.15 mmol) is treated with lithium hydroxide (0.16 g, 3.77 mmol) in methanol/tetrahydrofuran/water (1:1:1) (30 ml) at 0° C. After 2 hours, the mixture is slowly warmed to room temperature and stirred overnight. The reaction mixture is acidified with 1N hydrochloric acid (3.8 ml), diluted with water, and extracted with chloroform. The organic layer is dried over sodium sulfate and concentrated in vacuo to give N-(3,5-dimethyl benzoyl)-N-methyl-3-[4-(1,2,4-triazol-1-yl)-phenyl]-(D,L)-alanine.

(h) A mixture of 1,2,3-triazole (3.4 ml, 58.7 mmol), potassium carbonate (9.03 g, 65.4 mmol), and 4-fluorobenzaldehyde (6.3 ml, 58.7 mmol) in pyridine (30 ml) is heated under nitrogen atmosphere at reflux overnight. After pyridine is distilled, the mixture is diluted with methylene chloride, filtered and washed with chloroform. The combined filtrate is washed with water, dried over magnesium sulfate, and concentrated in vacuo. The crude material is purified by column chromatography on silica with hexane/ethyl acetate (5:1) to give 4-(1,2,3-triazol-1-yl)-benzaldehyde and with hexane/ethyl acetate (1:2) to give 4-(1,2,3-triazol-1-yl)-benzaldehyde.

To a solution of trimethyl 2-(3,5-dimethylbenzoyl)-amino-phosphonoacetate 0.53 g, 1.62 mmol) in methylene chloride (3.0 ml) under nitrogen atmosphere is added 1,8-diaza bicyclo[5.4.0]undec-7-ene (0.25 ml, 1.67 mmol). After 10 minutes, 4-(1,2,3-triazol-1-yl)-benzaldehyde (0.287 g, 1.66 mmol) is added and stirring is continued overnight. The reaction mixture is diluted with methylene chloride, washed with water, dried over magnesium sulfate, and concentrated in vacuo to give methyl 2-(3,5-dimethylbenzoyl)-amino-3-[4-(1,2,3-triazol-1-yl)phenyl]acrylate.

To a cooled (0° C.) solution of methyl 2-(3,5-dimethyl benzoyl) amino-3-[4-(1,2,3-triazol-1-yl)-phenyl]acrylate (0.351 g, 0.89 mmol) and iodomethane (0.18 ml, 2.89 mmol) in N,N'-dimethyl-formamide (3.0 ml) under nitrogen atmosphere is added sodium hydride (0.04 g 60% in oil, 1.0 mmol). The stirring is continued for 1.5 hours. The reaction mixture is diluted with diethyl ether, washed with water and with brine. The organic layer is dried over magnesium sulfate, concentrated in vacuo. The residue is purified by column chromatography on silica with hexane/ethyl acetate (1:1) to give methyl 2-[N-(3,5-dimethylbenzoyl)-N-methyl] amino-3-[4-(1,2,3-triazol-1-yl)phenyl]acrylate.

A solution of methyl 2-[N-(3,5-dimethylbenzoyl)-N-methyl]amino-3-[4-(1,2,3-triazol-1-yl)-phenyl]acrylate (0.275 g, 0.704 mmol) and trifluoroacetic acid (1.0 ml) in methanol (30 ml) is hydrogenated over palladium on carbon (10%, 80 mg) under 3atm hydrogen atmosphere. After 4 days, catalyst is removed by filtration and the filtrate is concentrated in vacuo. The residue is diluted with saturated sodium bicarbonate and extracted with ethyl acetate. The organic layer is washed with water and with brine, dried over magnesium sulfate, and concentrated in vacuo to give N-(3, 5-dimethylbenzoyl)-N-methyl-3-[4-(1,2,3-triazol-1-yl)-phenyl]-(D,L)-alanine methyl ester.

N-(3,5-Dimethylbenzoyl)-N-methyl-3-[4-(1,2,3-triazol-1-yl)-phenyl]-(D,L)-alanine methyl ester (0.248 g, 0.632 mmol) is treated with lithium hydroxide (0.037 g, 0.88 mmol) in methanol/tetrahydrofuran/water (2:1:2) (5 ml) at room temperature. After 1.5 hours, the reaction mixture is acidified with 1N hydrochloric acid (0.9 ml), diluted with water, and extracted with ethyl acetate. The organic layer is washed with brine, dried over magnesium sulfate, and concentrated in vacuo to give N-(3,5-dimethylbenzoyl)-N-methyl-3-[4-(1,2,3-triazol-1-yl)-phenyl]-(D,L)-alanine.

EXAMPLE 6

Starting cyclic amino acids and derivatives (wherein Y in formula I is a cyclic group) are either known in the art or can be prepared by methods illustrated below.

(a) 4-Amino-4-(tetrahydro-4H-thiopyran)carboxylic acid can be prepared according to method described in J. Med. Chem. 21, 1070 (1978). Such can be converted to 4-(N-t-butoxycarbonylamino)-tetrahydro-4H-thiopyran)-4-(N-n-butanesulfonyl)carboxamide according to methodology in example 1.

A solution thereof (1.0 g, 2.6 mmole) in ethanol (25 mL) is treated with 32% peracetic acid in acetic acid (4.0 mL, 16.8 mmole) at room temperature. The reaction mixture is stirred at room temperature for 15 minutes and diluted with 300 mL 1:1 ethyl acetate/ether, washed with three portions of water (600 mL), washed once with 100 mL brine, dried over magnesium sulfate, filtered and concentrated in vacuo. Chromatography on silica using 1:1 ethyl acetate, hexane gives the sulfone, 4-(N-t-butoxycarbonylamino)-tetrahydro-4H-thiopyran-S-dioxide)-4-(N-n-butanesulfonyl)carboxamide, as a white solid.

(b) 4-Amino-4H-tetrahydropyran-4-carboxylic acid can be prepared as follows:

A mixture of tetrahydro-4H-pyran-4-one (15.0 g, 0.15 mole), sodium cyanide (22.0 g, 0.45 mole) and ammonium carbonate (216 g, 2.25 mole) in distilled water (500 mL) is stirred at 60° C. under $N_2$ for 24 hours. The reaction mixture is heated to reflux to destroy the excess ammonium carbonate. The solution is then evaporated down to a volume of 100 mL and cooled to 0° C. The white crystalline hydantoin is filtered and rinsed with two 50 ml portions of distilled water at 0° C.

A solution of the hydantoin (20.0 g, 0.12 mole) and barium hydroxide octahydrate (111 g, 0.35 mole) in distilled water (650 mL) is refluxed for 24 hours. Carbon dioxide gas is bubbled through the mixture until the pH is 7. The mixture is warmed to 50° C. and filtered to remove the barium carbonate. The clear solution is evaporated to dryness. The crude product is dissolved in a minimal amount of refluxing distilled water and filtered to remove more barium salts. The 4-amino-4H-tetrahydropyran-4-carboxylic acid crystallizes from the solution.

(c) 4-Ethylenedioxy-1-aminocyclohexane-1-carboxylic acid can be prepared as follows:

1,4-Cyclohexanedione mono-ethylene ketal (10.0 g, 64.0 mmol) is added in one portion to a suspension of ammonium carbonate (24.8 g, 258 mmol) and sodium cyanide (6.3 g, 129 mmol) in water (150 mL). Ethyl alcohol (150 mL) is added, and the suspension is heated at 60° C. for 20 hours. After cooling to room temperature, the mixture is concentrated in vacuo to one-half the original volume. The suspension is filtered, and the precipitate is washed well with water, then dried in vacuo to give 9,12-dioxa-1,3-diaza dispiro[4.2.4.2]tetra-decane-2,4-trione as a white solid.

A solution of 9,12-dioxa-1,3-diazadispiro[4.2.4.2]tetra-decane-2,4-trione (1.05 g, 4.6 mmol) in 0.5 N sodium hydroxide (50 mL) is refluxed for 18 hours. The solution is concentrated in vacuo to one-half the original volume and acidified to pH=7 with concentrated hydrochloric acid. The resulting suspension is filtered, and the filtrate is acidified to pH=4 with 1N hydrochloric acid and concentrated in vacuo to give 1,4-dioxaspiro[4.5]decane-8-amino-8-carboxylic acid (4-ethylenedioxy-1-aminocyclohexane-1-carboxylic acid) as a white solid.

EXAMPLE 7

Prepared similarly to e.g. example 1 starting with 5-(a-aminopropanoic acid tert-butyl ester)-2-phenylpyrimidine of example 5(c) is the compound of formula I wherein Ar is 3,5-dimethylphenyl, $R_1$ is methyl, $R_2$ is hydrogen, $R_3$ is 2-phenyl-5-pyrimidinylmethyl, Y is 4-(tetrahydro-4H-pyranylidenyl) and R is $CONH-SO_2-(CH_2)_3CH_3$.

EXAMPLE 8

Prepared similarly to e.g. example 1 is the compound of formula I wherein Ar is 3,5-dimethylphenyl, $R_1$ and $R_2$ together represent propylene (to form a pyrrolidine ring together with the carbon and nitrogen atoms to which such is attached), Y is 4-tetrahydro-4H-pyranylidene and R is $CONH-SO_2-(CH_2)_3CH_3$. The starting material for condensation with 4-amino-4H-tetrahydropyran-4-N-(n-butanesulfonyl)carboxamide is prepared as follows:

To a −78° C. solution of lithium bis(trimethylsilylamide) (8 mL, 8 mmol) in THF is slowly added N-(3,5-dimethylbenzoyl)proline methyl ester (1.0 g, 3.8 mmol). After 20 minutes p-(1-pyrrolyl)-benzyl bromide (950 mg) in 5 mL of THF is added over a 5 minute period. The solution is warmed to room temperature, quenched with acetic acid and concentrated under reduced pressure. The residue is extracted with EtOAc. The organic layer is washed with $NH_4Cl$ (sat.), $NaHCO_3$ solution, dried ($MgSO_4$) and chromatographed on silica gel eluting with hexane/ethyl acetate (3:1) giving N-(3,5-dimethylbenzoyl)-2-[p-(1-pyrrolyl)-benzyl]-proline methyl ester.

EXAMPLE 9

| Pharmaceutical Composition (for 10,000 tablets) | |
| --- | --- |
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

What is claimed is:

1. A compound of the formula

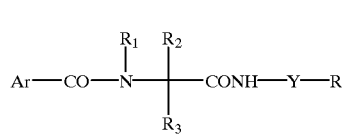

(I)

wherein R is carboxy, esterified carboxy, carbamoyl, N-(alkyl or aryl)-carbamoyl, cyano, 5-tetrazolyl or $CONH-SO_2R_4$;

$R_1$ is hydrogen, lower alkyl, aryl-lower alkyl or cycloalkyl-lower alkyl;

$R_2$ is hydrogen or lower alkyl, or $R_1$ and $R_2$ represent lower alkylene to form together with the carbon and nitrogen atoms to which they are attached an azacycloalkane ring;

$R_3$ is heterocyclic or carbocyclic (aryl or biaryl)-lower alkyl;

Y is lower alkylidenyl, 3–10-membered cycloalkylidenyl which may be substituted by oxo, alkylenedioxy, hydroxy, acyloxy, lower alkoxy; or Y is 5–10-membered cycloalkylidenyl fused to a saturated or unsaturated carbocyclic 5–6-membered ring; or Y is 5- to 8-membered oxacycloalkylidenyl, 5- to 8-membered (thia-, oxothia- or dioxothia-) cycloalkylidenyl, or 5- to 8-membered azacycloalkylidenyl optionally N-substituted by lower alkyl or aryl-lower alkyl;

$R_4$ represents hydrogen, lower alkyl, carbocyclic aryl, heterocyclic aryl, cycloalkyl, (carbocyclic aryl, heterocyclic aryl, cycloalkyl, hydroxy, acyloxy, or lower alkoxy)-lower alkyl, lower alkyl substituted by carboxyl, by esterified carboxyl or by amidated carboxyl; and Ar represents carbocyclic or heterocyclic aryl; provided that R is cyano, 5-tetrazolyl or CONH—SO$_2$R$_4$ when Y is lower alkylidenyl; or a pharmaceutically acceptable salt thereof.

2. A compound according to claim 1 wherein

R is carboxy, 5-tetrazolyl, esterified carboxy or CONH—SO$_2$—R$_4$;

R is C$_1$–C$_4$-alkyl;

R$_2$ hydrogen; or

R$_1$ and R$_2$ together represent C$_3$–C$_5$alkylene;

R$_3$ is monocyclic carbocyclic or heterocyclic aryl-lower alkyl or biaryl-lower alkyl in which biaryl is monocyclic carbocyclic or heterocyclic aryl substituted by monocyclic carbocyclic or heterocyclic aryl;

Y is 3–10-membered cycloalkylidenyl or 5–10-membered cycloalkylidenyl fused to an unsaturated carbocyclic 6 membered ring, 5–8 membered oxacycloalkylidenyl, or 5–8-membered (thia, oxothia or dioxothia)-cycloalkylidenyl;

R$_4$ represents monocyclic carbocyclic aryl, monocyclic carbocyclic aryl-lower alkyl, lower alkyl, cycloalkyl, carboxy-lower alkyl or lower alkoxycarbonyl-lower alkyl; and p1 Ar is carbocyclic or heterocyclic monocyclic aryl;

or a pharmaceutically acceptable salt thereof.

3. A compound according to claim 2 wherein

R is carboxy, 5-tetrazolyl, lower alkoxycarbonyl or CONH—SO$_2$—R$_4$;

R$_1$ is C$_1$–C$_3$-alkyl;

R$_2$ is hydrogen; or

R$_1$ and R$_2$ together represent propylene or butylene;

R$_3$ is monocyclic carbocyclic or heterocyclic aryl-methyl, or biaryl-methyl in which biaryl is biphenyl, pyridylphenyl, thienylphenyl, furylphenyl, pyrrolylphenyl, imidazolylphenyl, oxazolylphenyl, isoxazolylphenyl, thiazolylphenyl, isothiazolylphenyl, thiazolylphenyl, tetrazolylphenyl or phenylpyrimidinyl; or a pharmaceutically acceptable salt thereof;

Y is cyclopropylidenyl, cyclopentylidenyl, indanylidenyl, 4-tetrahydro-4H-pyranylidenyl, cyclohexylidenyl, 4-tetrahydro-4H-thiopyranylidenyl, 4-ethylenedioxycyclohexylidenyl or 4-oxocyclohexylidenyl;

R$_4$ is lower alkyl, phenyl, benzyl, lower alkoxycarbonyl-lower alkyl or carboxy-lower alkyl;

Ar is monocyclic carbocyclic aryl;

or a pharmaceutically acceptable salt thereof.

4. A compound according to claim 2 wherein

R is carboxy, lower alkoxycarbonyl or CONHSO$_2$—R$_4$;

R$_1$ is methyl;

R$_2$ is hydrogen;

R$_3$ is 4-pyrrolidinobenzyl, 4-piperidinobenzyl, 4-(1-pyrrolyl)-benzyl, 4-(5-isoxazolyl)benzyl, 4-(3-thienyl) benzyl, 4-(2-thienyl)-benzyl, 4-biphenylylmethyl or 4-(2-pyridyl)benzyl;

Y has meaning as defined in said claim;

R$_4$ is lower alkyl or cycloalkyl;

Ar is phenyl or phenyl substituted by one or two substituents being lower alkyl, halogen, hydroxy, trifluoromethyl or lower alkyl; or Ar is pyridyl or pyridyl substituted by lower alkyl; or a pharmaceutically acceptable salt thereof.

5. A compound according to claim 2 wherein R is CONH—SO$_2$—R$_4$.

6. A compound according to claim 2 wherein R is carboxy, esterified carboxy or 5-tetrazolyl.

7. A compound according to claim 2 wherein R is CONH—SO$_2$—R$_4$ and R$_4$ is lower alkyl.

8. A compound according to claim 2 wherein R$_3$ is biarylmethyl.

9. A compound according to claim 2 of the formula

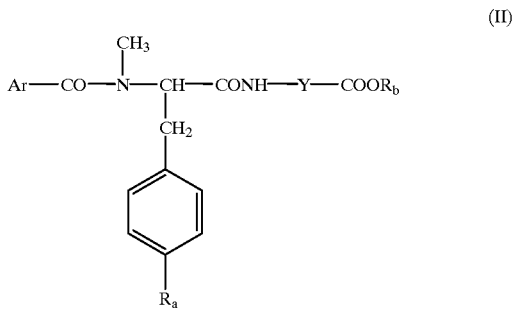

(II)

wherein Ar is phenyl optionally substituted by one or two of lower alkyl, halo, hydroxy, lower alkoxy or trifluoromethyl;

R$_a$ is 1-pyrrolyl, 5-isoxazolyl, 2-thienyl, 3-thienyl or phenyl;

R$_b$ is hydrogen, lower alkyl or aryl-lower alkyl;

Y is cyclopropylidenyl, cyclopentylidenyl, indanylidenyl, 4-tetrahydro-4H-pyranylidenyl, cyclo hexylidenyl, 4-tetrahydro-4H-thiopyranylidenyl, or 4-ethylenedioxy-1-cyclohexylidenyl;

or a pharmaceutically acceptable salt thereof.

10. A compound according to claim 2 of the formula

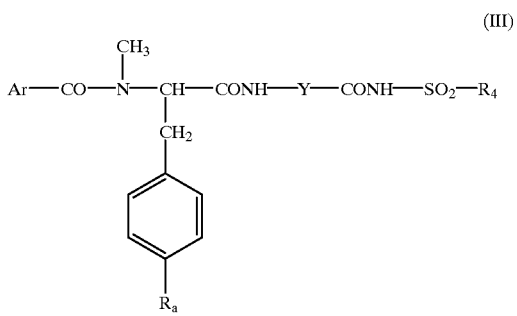

(III)

wherein Ar is phenyl optionally substituted by one or two of lower alkyl, halo, hydroxy, lower alkoxy or trifluoromethyl;

R$_a$ is 1-pyrrolyl, 5-isoxazolyl, 2-thienyl, 3-thienyl or phenyl; and

R$_4$ is lower alkyl;

Y is cyclopropylidenyl, cyclopentylidenyl, indanylidenyl, 4-tetra hydro-4H-pyranylidenyl, cyclohexylidenyl, 4-tetrahydro-4H-thio-pyranylidenyl, or 4-ethylenedioxy-1-cyclohexylidenyl;

or a pharmaceutically acceptable salt thereof.

11. A compound according to claim 9 wherein Ar is 3,5-dimethylphenyl, R$_a$ is 1-pyrrolyl, Y is cyclopropylidenyl and R$_b$ is hydrogen; or a pharmaceutically acceptable salt thereof.

12. A compound according to claim 10 wherein Ar is 3,5-dimethylphenyl, $R_a$ is 1-pyrrolyl, Y is cyclopropylidenyl, and $R_4$ is n-butyl; or a pharmaceutically acceptable salt thereof.

13. A compound according to claim 10 wherein Ar is 3,5-dimethylphenyl, $R_a$ is 1-pyrrolyl, Y is 4-tetrahydro-4H-pyranylidenyl and $R_4$ is n-butyl; or a pharmaceutically acceptable salt thereof.

14. An endothelin antagonist pharmaceutical composition comprising an effective endothelin antagonist amount of a compound of claim 1 in combination with one or more pharmaceutically acceptable carriers.

15. A method of inhibiting endothelin activity in mammals which comprises administering to a mammal in need thereof an effective endothelin antagonist amount of a compound of claim 1.

16. A method of treating endothelin dependent disorders in mammals which comprises administering to a mammal in need thereof an effective endothelin antagonist amount of a compound of claim 1.

17. A method according to claim 16 of treating cardiovascular and bronchial disorders.

* * * * *

UNITED STATES PATENT AND TRADEMARK OFFICE
CERTIFICATE OF CORRECTION

PATENT NO. : 5,977,075

DATED : November 2, 1999

INVENTOR(S) : Ksander, et al

It is certified that error appears in the above-identified patent and that said Letters Patent is hereby corrected as shown below:

Signed and Sealed this

Third Day of April, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 5,977,075  
DATED : November 2, 1999  
INVENTOR(S) : Ksander et al.

Page 1 of 1

It is certified that error appears in the above-identified patent and that said Letters Patent is hereby corrected as shown below:

Column 29, claim 2,  
Line 11, claim 2, should read -- $R_1$ is $C_1$-$C_4$-alkyl; --

Column 29, claim 2,  
Line 26, should read -- alkyl; and Ar is carbocyclic or heterocylic mono --

This certificate supersedes Certificate of Correction issued April 3, 2001.

Signed and Sealed this

Nineteenth Day of February, 2002

Attest:

Attesting Officer

JAMES E. ROGAN  
Director of the United States Patent and Trademark Office

UNITED STATES PATENT AND TRADEMARK OFFICE
CERTIFICATE OF CORRECTION

PATENT NO. : 5,977,075
DATED : November 2, 1999
INVENTOR(S) : Ksander et al.

Page 1 of 1

It is certified that error appears in the above-identified patent and that said Letters Patent is hereby corrected as shown below:

Column 29, claim 2,
Line 11, should read -- $R_1$ is $C_1$-$C_4$-alkyl; --

Column 29, claim 2,
Line 26, should read -- alkyl; and Ar is carbocyclic or heterocxclic mono --

This certificate supersedes Certificate of Correction issued February 19, 2002.

Signed and Sealed this

Sixteenth Day of April, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

PATENT NO.   : 5,977,075
DATED        : November 2, 1999
INVENTOR(S)  : Ksander et al.

It is certified that error appears in the above-identified patent and that said Letters Patent is hereby corrected as shown below:

<u>Column 29,</u>
Line 11, should read -- $R_1$ is $C_1$-$C_4$-alkyl; --

<u>Column 29,</u>
Line 26, should read -- alkyl; and Ar is carbocyclic or heterocyclic mono --

This certificate supersedes Certificate of Correction issued April 16, 2002.

Signed and Sealed this

Twentieth Day of August, 2002

Attest:

Attesting Officer

JAMES E. ROGAN
*Director of the United States Patent and Trademark Office*